US011376168B2

(12) United States Patent
Bewick-Sonntag et al.

(10) Patent No.: US 11,376,168 B2
(45) Date of Patent: Jul. 5, 2022

(54) ABSORBENT ARTICLE WITH ABSORBENT STRUCTURE HAVING ANISOTROPIC RIGIDITY

(71) Applicant: The Procter & Gamble Company, Cincinnati, OH (US)

(72) Inventors: Christopher Philip Bewick-Sonntag, Cincinnati, OH (US); Clint Adam Morrow, Union, KY (US); Dean Larry DuVal, Lebanon, OH (US); Wade Monroe Hubbard, Jr., Wyoming, OH (US); Remo Bellucci, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 837 days.

(21) Appl. No.: 15/344,221

(22) Filed: Nov. 4, 2016

(65) Prior Publication Data

US 2017/0119594 A1    May 4, 2017

Related U.S. Application Data

(60) Provisional application No. 62/250,825, filed on Nov. 4, 2015.

(51) Int. Cl.
*A61F 13/53* (2006.01)
*A61F 13/15* (2006.01)
(Continued)

(52) U.S. Cl.
CPC ........ *A61F 13/53* (2013.01); *A61F 13/15203* (2013.01); *A61F 13/534* (2013.01);
(Continued)

(58) Field of Classification Search
CPC .. A61F 13/15203; A61F 13/53; A61F 13/534; A61F 2013/15357; A61L 15/425; A61L 15/60
See application file for complete search history.

(56) References Cited

U.S. PATENT DOCUMENTS 1,688,341 A    10/1928   Howard
2,615,389 A    10/1952   Huebner
(Continued)

FOREIGN PATENT DOCUMENTS

CA    2250138        3/1997
CA    2331036 A1    11/1999
(Continued)

OTHER PUBLICATIONS

PCT International Search Report, PCT/US2015/037943, dated Aug. 26, 2015, 9 pages.
(Continued)

*Primary Examiner* — Michele M Kidwell
(74) *Attorney, Agent, or Firm* — William E. Gallagher

(57) ABSTRACT

An Absorbent article comprising a topsheet, a backsheet, and an absorbent core comprising an absorbent structure, wherein the absorbent structure exhibits a Cross Direction bending rigidity between 0.3 gf*cm^2/cm and 1.6 gf*cm^2/cm and a Machine Direction bending rigidity between 1.5 gf*cm^2/cm and 14 gf*cm^2/cm.

11 Claims, 2 Drawing Sheets

(51) Int. Cl.
*A61F 13/534* (2006.01)
*A61L 15/42* (2006.01)
*A61L 15/60* (2006.01)

(52) U.S. Cl.
CPC ............ *A61L 15/425* (2013.01); *A61L 15/60* (2013.01); *A61F 2013/15357* (2013.01); *A61F 2013/530839* (2013.01); *A61F 2013/530905* (2013.01)

(56) References Cited

U.S. PATENT DOCUMENTS

| | | |
|---|---|---|
| 2,734,224 A | 2/1956 | Winstead |
| 2,894,732 A | 7/1959 | Taber et al. |
| 3,122,142 A | 2/1964 | Crowe, Jr. |
| 3,229,691 A | 1/1966 | Crowe, Jr. |
| 3,274,046 A | 9/1966 | Shannon et al. |
| 3,286,992 A | 11/1966 | Armeniades et al. |
| 3,381,336 A | 5/1968 | Wells |
| 3,525,338 A | 8/1970 | Bernardin |
| 3,546,055 A | 12/1970 | Spertus |
| 3,598,742 A | 8/1971 | Jamison et al. |
| 3,617,594 A | 11/1971 | Willy |
| 3,620,506 A | 11/1971 | So |
| 3,669,103 A | 6/1972 | Harper et al. |
| 3,669,823 A | 6/1972 | Wood |
| 3,670,731 A | 6/1972 | Harmon |
| 3,683,921 A | 8/1972 | Brooks et al. |
| 3,704,006 A | 11/1972 | Grout et al. |
| 3,804,700 A | 4/1974 | Hoey |
| 3,815,601 A | 6/1974 | Schaefer |
| 3,865,352 A | 2/1975 | Nelson et al. |
| 3,884,000 A | 5/1975 | Faleij |
| 3,908,645 A | 9/1975 | Sandvig |
| 3,982,374 A | 9/1976 | Schaefer |
| 3,994,298 A | 11/1976 | Des |
| 4,019,719 A | 4/1977 | Schuster et al. |
| 4,026,292 A | 5/1977 | Hutchins et al. |
| 4,051,065 A | 9/1977 | Venema |
| 4,055,184 A | 10/1977 | Karami |
| 4,061,145 A | 12/1977 | Desmarais |
| 4,061,313 A | 12/1977 | Brauner et al. |
| 4,062,524 A | 12/1977 | Brauner et al. |
| 4,096,303 A | 6/1978 | Doerfling |
| 4,110,276 A | 8/1978 | Desmarais |
| 4,211,277 A | 7/1980 | Grosz-Roll et al. |
| 4,321,924 A | 3/1982 | Ahr |
| 4,338,366 A | 7/1982 | Evans et al. |
| 4,357,386 A | 11/1982 | Luciano et al. |
| 4,381,783 A | 5/1983 | Elias |
| 4,416,201 A | 11/1983 | Kessler |
| 4,425,130 A | 1/1984 | Desmarais |
| 4,450,833 A | 5/1984 | Brooks et al. |
| 4,473,611 A | 9/1984 | Haq |
| 4,535,021 A | 8/1985 | Friedrich |
| 4,537,819 A | 8/1985 | Schortmann et al. |
| 4,538,920 A | 9/1985 | Drake |
| 4,550,681 A | 11/1985 | Zimmer et al. |
| 4,589,876 A | 5/1986 | Van Tilburg |
| 4,606,958 A | 8/1986 | Haq et al. |
| 4,664,662 A | 5/1987 | Webster |
| 4,673,402 A | 6/1987 | Weisman |
| 4,689,118 A | 8/1987 | Makoui et al. |
| 4,689,258 A | 8/1987 | Slosberg et al. |
| 4,725,628 A | 2/1988 | Garvey et al. |
| 4,737,582 A | 4/1988 | Goldman et al. |
| 4,740,700 A | 4/1988 | Shaham et al. |
| 4,758,098 A | 7/1988 | Meyer |
| 4,758,466 A | 7/1988 | Dabi et al. |
| 4,761,203 A | 8/1988 | Vinson |
| 4,806,288 A | 2/1989 | Nowosinski et al. |
| 4,865,596 A | 9/1989 | Weisman et al. |
| 4,875,974 A | 10/1989 | Rich |
| 4,892,535 A | 1/1990 | Bjoemberg et al. |
| 4,923,454 A | 5/1990 | Seymour |
| 4,935,022 A | 6/1990 | Lash et al. |
| 4,950,264 A | 8/1990 | Osborn, III |
| 4,988,344 A | 1/1991 | Reising et al. |
| 4,988,345 A | 1/1991 | Reising |
| 4,994,037 A | 2/1991 | Bernardin |
| 5,004,760 A | 4/1991 | Patton et al. |
| 5,037,859 A | 8/1991 | Williams, Jr. et al. |
| 5,059,629 A | 10/1991 | Patton et al. |
| 5,134,007 A | 7/1992 | Reising et al. |
| 5,147,345 A | 9/1992 | Lavon |
| 5,149,334 A | 9/1992 | Berg et al. |
| 5,149,720 A | 9/1992 | Desmarais et al. |
| 5,160,345 A | 11/1992 | Bragg |
| 5,169,706 A | 12/1992 | Collier, IV et al. |
| 5,171,613 A | 12/1992 | Bok et al. |
| 5,175,046 A | 12/1992 | Nguyen |
| 5,192,606 A * | 3/1993 | Proxmire .......... A61F 13/49009 428/171 |
| 5,221,710 A | 6/1993 | Markusch et al. |
| 5,221,726 A | 6/1993 | Dabi et al. |
| 5,234,423 A | 8/1993 | Alemany et al. |
| 5,244,941 A | 9/1993 | Bruckbauer et al. |
| 5,246,855 A | 9/1993 | Katinger et al. |
| 5,248,309 A | 9/1993 | Serbiak |
| 5,260,345 A | 11/1993 | Desmarais |
| 5,287,707 A | 2/1994 | Kitayama |
| 5,306,734 A | 4/1994 | Bass et al. |
| 5,318,554 A | 6/1994 | Lavon et al. |
| 5,328,935 A | 7/1994 | Van et al. |
| 5,331,015 A | 7/1994 | Desmarais et al. |
| 5,338,766 A | 8/1994 | Phan et al. |
| 5,350,370 A | 9/1994 | Jackson et al. |
| 5,372,421 A | 12/1994 | Pardikes |
| 5,387,207 A | 2/1995 | Dyer |
| 5,397,316 A | 3/1995 | Young |
| 5,425,725 A | 6/1995 | Tanzer |
| 5,436,066 A | 7/1995 | Chen |
| 5,454,801 A | 10/1995 | Lauritzen |
| 5,454,910 A | 10/1995 | Yoon et al. |
| 5,460,622 A | 10/1995 | Dragoo et al. |
| 5,462,538 A | 10/1995 | Korpman |
| 5,466,232 A | 11/1995 | Cadieux et al. |
| 5,486,410 A | 1/1996 | Groeger et al. |
| 5,487,736 A | 1/1996 | Van |
| 5,500,451 A | 3/1996 | Goldman et al. |
| 5,506,035 A | 4/1996 | Van et al. |
| 5,518,801 A | 5/1996 | Chappell |
| 5,520,460 A | 5/1996 | Lantz |
| 5,536,264 A | 7/1996 | Hsueh et al. |
| 5,550,167 A | 8/1996 | Desmarais |
| 5,560,878 A | 10/1996 | Dragoo et al. |
| 5,562,646 A | 10/1996 | Goldman |
| 5,564,827 A | 10/1996 | Signer |
| 5,571,849 A | 11/1996 | Desmarais |
| 5,573,994 A | 11/1996 | Kabra et al. |
| 5,580,348 A | 12/1996 | Blaney et al. |
| 5,583,162 A | 12/1996 | Li et al. |
| 5,599,335 A | 2/1997 | Goldman |
| 5,607,550 A | 3/1997 | Akers |
| 5,620,252 A | 4/1997 | Maurer |
| 5,638,752 A | 6/1997 | Hartung et al. |
| 5,639,070 A | 6/1997 | Deckard |
| 5,647,862 A | 7/1997 | Osborn, III et al. |
| 5,647,863 A | 7/1997 | Hammons et al. |
| 5,650,222 A | 7/1997 | Desmarais et al. |
| 5,651,862 A | 7/1997 | Anderson et al. |
| 5,653,922 A | 8/1997 | Li et al. |
| 5,692,939 A | 12/1997 | Desmarais |
| 5,713,881 A | 2/1998 | Rezai et al. |
| 5,722,482 A | 3/1998 | Buckley |
| 5,730,738 A | 3/1998 | Mcfall et al. |
| 5,732,323 A | 3/1998 | Nyrhila |
| 5,741,581 A | 4/1998 | Desmarais et al. |
| 5,744,506 A | 4/1998 | Goldman et al. |
| 5,813,762 A | 9/1998 | Fleischli et al. |
| 5,817,704 A | 10/1998 | Shiveley et al. |
| 5,827,909 A | 10/1998 | Desmarais |
| 5,856,366 A | 1/1999 | Shiveley et al. |
| 5,858,292 A | 1/1999 | Dragoo et al. |

(56) References Cited

U.S. PATENT DOCUMENTS

| | | | |
|---|---|---|---|
| 5,863,957 | A | 1/1999 | Li et al. |
| 5,868,724 | A | 2/1999 | Dierckes, Jr. et al. |
| 5,869,171 | A | 2/1999 | Shiveley et al. |
| 5,873,869 | A | 2/1999 | Hammons et al. |
| 5,900,437 | A | 5/1999 | Mitchell et al. |
| 5,904,672 | A | 5/1999 | Lemahieu et al. |
| 5,938,328 | A | 8/1999 | Pinto et al. |
| 5,948,829 | A | 9/1999 | Wallajapet et al. |
| 5,962,068 | A | 10/1999 | Tsuchiya et al. |
| 5,971,603 | A | 10/1999 | Davis et al. |
| 6,027,795 | A | 2/2000 | Kabra et al. |
| 6,042,575 | A | 3/2000 | Osborn, III et al. |
| 6,046,377 | A | 4/2000 | Huntoon et al. |
| 6,083,211 | A | 7/2000 | Desmarais |
| 6,103,645 | A | 8/2000 | Chang et al. |
| 6,107,538 | A | 8/2000 | Young et al. |
| 6,109,781 | A | 8/2000 | Ogasawara et al. |
| 6,132,803 | A | 10/2000 | Kelly et al. |
| 6,162,961 | A | 12/2000 | Tanner et al. |
| 6,174,929 | B1 | 1/2001 | Haehnle et al. |
| 6,183,587 | B1 | 2/2001 | Mcfall et al. |
| 6,203,654 | B1 | 3/2001 | Mcfall et al. |
| 6,231,556 | B1 | 5/2001 | Osborn, III |
| 6,241,713 | B1 | 6/2001 | Gross et al. |
| 6,251,479 | B1 | 6/2001 | Groitzsch et al. |
| 6,261,335 | B1 | 7/2001 | Kern et al. |
| 6,261,679 | B1 | 7/2001 | Chen et al. |
| 6,277,104 | B1 | 8/2001 | Lasko et al. |
| 6,316,688 | B1 | 11/2001 | Hammons |
| 6,372,953 | B1 | 4/2002 | Young et al. |
| 6,399,854 | B1 | 6/2002 | Vartiainen |
| 6,410,820 | B1 | 6/2002 | Mcfall et al. |
| 6,426,445 | B1 | 7/2002 | Young et al. |
| 6,455,600 | B1 | 9/2002 | Haehnle et al. |
| 6,475,199 | B1 | 11/2002 | Gann et al. |
| 6,486,379 | B1 | 11/2002 | Chen et al. |
| 6,503,233 | B1 | 1/2003 | Chen |
| 6,525,106 | B1 | 2/2003 | Desmarais et al. |
| 6,551,295 | B1 | 4/2003 | Schmidt et al. |
| 6,570,057 | B1 | 5/2003 | Schmidt et al. |
| 6,582,411 | B1 | 6/2003 | Carstens et al. |
| 6,590,136 | B1 | 7/2003 | Young et al. |
| 6,600,086 | B1 | 7/2003 | Mace et al. |
| 6,603,054 | B2 | 8/2003 | Chen et al. |
| 6,642,430 | B1 | 11/2003 | Busam et al. |
| 6,657,101 | B1 | 12/2003 | Malmgren et al. |
| 6,664,439 | B1 | 12/2003 | Arndt et al. |
| 6,673,057 | B1 | 1/2004 | Ehrnsperger et al. |
| 6,673,981 | B1 | 1/2004 | Stroembom |
| 6,676,892 | B2 | 1/2004 | Das et al. |
| 6,689,935 | B2 | 2/2004 | Chen et al. |
| 6,706,775 | B2 | 3/2004 | Hermann et al. |
| 6,713,661 | B1 | 3/2004 | Arndt et al. |
| 6,720,471 | B1 | 4/2004 | Arndt et al. |
| 6,749,413 | B2 | 6/2004 | Fare |
| 6,800,666 | B2 | 10/2004 | Haehnle et al. |
| 6,811,842 | B1 | 11/2004 | Ehrnsperger et al. |
| 6,855,424 | B1 | 2/2005 | Thomas et al. |
| 6,943,200 | B1 | 9/2005 | Corrand et al. |
| 6,969,548 | B1 | 11/2005 | Goldfine |
| 6,989,005 | B1 | 1/2006 | Lavon et al. |
| 6,989,075 | B1 | 1/2006 | Kao et al. |
| 7,056,404 | B2 | 6/2006 | Mcfall et al. |
| 7,172,801 | B2 | 2/2007 | Hoying et al. |
| 7,189,888 | B2 | 3/2007 | Wang et al. |
| 7,198,742 | B2 | 4/2007 | Gerndt |
| 7,235,708 | B2 | 6/2007 | Guidotti et al. |
| 7,285,576 | B2 | 10/2007 | Hyde et al. |
| 7,410,683 | B2 | 8/2008 | Curro et al. |
| 7,462,756 | B2 | 12/2008 | Malowaniec |
| 7,507,459 | B2 | 3/2009 | Turner et al. |
| 7,553,532 | B2 | 6/2009 | Turner et al. |
| 7,575,635 | B2 | 8/2009 | Perttilae et al. |
| 7,648,752 | B2 | 1/2010 | Hoying et al. |
| 7,682,686 | B2 | 3/2010 | Curro et al. |
| 7,718,243 | B2 | 5/2010 | Curro et al. |
| 7,732,657 | B2 | 6/2010 | Hammons et al. |
| 7,735,522 | B2 | 6/2010 | Bivin et al. |
| 7,754,050 | B2 | 7/2010 | Redd et al. |
| 7,789,994 | B2 | 9/2010 | Hupp et al. |
| 7,838,099 | B2 | 11/2010 | Curro et al. |
| 7,838,723 | B1 | 11/2010 | Schmidt et al. |
| 7,850,672 | B2 | 12/2010 | Guidotti et al. |
| 7,935,207 | B2 | 5/2011 | Zhao et al. |
| 8,124,827 | B2 | 2/2012 | Tamburro et al. |
| 8,143,472 | B1 | 3/2012 | Bragd et al. |
| 8,153,226 | B2 | 4/2012 | Curro |
| 8,163,132 | B2 | 4/2012 | Kien |
| 8,207,393 | B2 | 6/2012 | Bach |
| 8,263,820 | B2 | 9/2012 | Carlucci et al. |
| 8,410,016 | B2 | 4/2013 | Cote et al. |
| 8,426,670 | B2 | 4/2013 | Nagasuna et al. |
| 8,641,267 | B2 | 2/2014 | Baeuerle et al. |
| 8,674,169 | B2 | 3/2014 | Brennan et al. |
| 8,707,717 | B2 | 4/2014 | Fox et al. |
| 8,708,723 | B2 | 4/2014 | Stoltz et al. |
| 8,728,049 | B2 | 5/2014 | Hammons et al. |
| 8,906,404 | B2 | 12/2014 | Wellings |
| 9,408,761 | B2 | 8/2016 | Xu et al. |
| 9,566,196 | B2 | 2/2017 | Carlucci et al. |
| 9,907,709 | B2 | 3/2018 | Seitz et al. |
| 9,956,586 | B2 | 5/2018 | Pinyayev et al. |
| 9,974,424 | B2 | 5/2018 | Roe et al. |
| 9,993,836 | B2 | 6/2018 | Mcneil et al. |
| 10,016,779 | B2 | 7/2018 | Mcneil et al. |
| 10,028,867 | B2 | 7/2018 | Ehrnsperger et al. |
| 10,045,888 | B2 | 8/2018 | Strube et al. |
| 10,045,890 | B2 | 8/2018 | Hubbard, Jr. |
| 10,131,724 | B2 | 11/2018 | Merrigan et al. |
| 10,357,588 | B2 | 7/2019 | Thompson, Jr. et al. |
| 10,583,053 | B2 | 3/2020 | Robles et al. |
| 10,729,600 | B2 | 8/2020 | Bewick-sonntag et al. |
| 2001/0000796 | A1 | 5/2001 | Osborn et al. |
| 2001/0024716 | A1 | 9/2001 | Chen et al. |
| 2001/0033527 | A1 | 10/2001 | Smith |
| 2001/0041876 | A1 | 11/2001 | Creagan et al. |
| 2001/0047456 | A1 | 11/2001 | Schrobenhauzer et al. |
| 2002/0034911 | A1 | 3/2002 | Tsuchiya et al. |
| 2002/0057627 | A1 | 5/2002 | Schubert et al. |
| 2002/0064087 | A1 | 5/2002 | Catalfamo et al. |
| 2002/0095132 | A1 | 7/2002 | Ashton et al. |
| 2002/0099348 | A1 | 7/2002 | Ollivier et al. |
| 2002/0118598 | A1 | 8/2002 | Schuchardt |
| 2002/0123283 | A1 | 9/2002 | Dyer et al. |
| 2002/0132106 | A1 | 9/2002 | Dyer et al. |
| 2002/0143310 | A1 | 10/2002 | Malmgren et al. |
| 2002/0177831 | A1 | 11/2002 | Daley et al. |
| 2003/0008108 | A1 | 1/2003 | Shizuno et al. |
| 2003/0015003 | A1 | 1/2003 | Fisler et al. |
| 2003/0084788 | A1 | 5/2003 | Fraser |
| 2003/0093050 | A1 | 5/2003 | Baker |
| 2003/0097103 | A1 | 5/2003 | Horney |
| 2003/0120231 | A1 | 6/2003 | Wang |
| 2003/0134918 | A1 | 7/2003 | Ko et al. |
| 2003/0165080 | A1 | 9/2003 | Pinyayev et al. |
| 2003/0181884 | A1 | 9/2003 | Carstens et al. |
| 2003/0191204 | A1 | 10/2003 | Hermann et al. |
| 2003/0211248 | A1 | 11/2003 | Ko et al. |
| 2003/0220039 | A1 | 11/2003 | Chen et al. |
| 2004/0037161 | A1 | 2/2004 | Honda et al. |
| 2004/0054341 | A1 | 3/2004 | Kellenberger et al. |
| 2004/0054342 | A1 | 3/2004 | Newbill et al. |
| 2004/0121905 | A1 | 6/2004 | Ranganathan et al. |
| 2004/0159616 | A1 | 8/2004 | Cohee et al. |
| 2004/0193129 | A1 | 9/2004 | Guidotti et al. |
| 2004/0199134 | A1 | 10/2004 | Mizutani et al. |
| 2004/0204554 | A1 | 10/2004 | Ko et al. |
| 2004/0214961 | A1 | 10/2004 | Gartner et al. |
| 2004/0218469 | A1 | 11/2004 | Unterlander et al. |
| 2004/0227275 | A1 | 11/2004 | Maschino et al. |
| 2004/0229008 | A1 | 11/2004 | Hoying |
| 2004/0242097 | A1 | 12/2004 | Hasenoehrl |
| 2005/0087292 | A1 | 4/2005 | Mcfall et al. |
| 2005/0123726 | A1 | 6/2005 | Broering et al. |

(56) References Cited

U.S. PATENT DOCUMENTS

| | | |
|---|---|---|
| 2005/0125923 A1 | 6/2005 | Benjamin et al. |
| 2005/0136224 A1 | 6/2005 | Nickel et al. |
| 2005/0185508 A1 | 8/2005 | Schulz-hanke et al. |
| 2005/0250866 A1 | 11/2005 | Champ et al. |
| 2005/0266230 A1 | 12/2005 | Hill et al. |
| 2006/0008419 A1 | 1/2006 | Hissink et al. |
| 2006/0052269 A1 | 3/2006 | Panandiker et al. |
| 2006/0058750 A1 | 3/2006 | Di et al. |
| 2006/0121811 A1 | 6/2006 | Mangold et al. |
| 2006/0127498 A1 | 6/2006 | Sugiura |
| 2006/0189240 A1 | 8/2006 | Taylor et al. |
| 2006/0193985 A1 | 8/2006 | Mcneil et al. |
| 2006/0286343 A1 | 12/2006 | Curro |
| 2007/0027435 A1 | 2/2007 | Nakagawa et al. |
| 2007/0043330 A1 | 2/2007 | Lankhof |
| 2007/0088308 A1 | 4/2007 | Ehrnsperger et al. |
| 2007/0116926 A1 | 5/2007 | Hoying et al. |
| 2007/0142803 A1 | 6/2007 | Soerens et al. |
| 2007/0225669 A1 | 9/2007 | Dyer |
| 2008/0056064 A1 | 3/2008 | Tanaka |
| 2008/0076844 A1 | 3/2008 | Van et al. |
| 2008/0217809 A1 | 9/2008 | Zhao |
| 2008/0221538 A1 | 9/2008 | Zhao |
| 2008/0281287 A1 | 11/2008 | Marcelo et al. |
| 2009/0036851 A1 | 2/2009 | Carlucci |
| 2009/0036854 A1 | 2/2009 | Guidotti et al. |
| 2009/0079107 A1 | 3/2009 | Abiru |
| 2009/0103393 A1 | 4/2009 | Moser et al. |
| 2009/0118689 A1 | 5/2009 | Lawson et al. |
| 2009/0122638 A1 | 5/2009 | Sato et al. |
| 2009/0266478 A1 | 10/2009 | Schafer et al. |
| 2009/0270827 A1 | 10/2009 | Gundersen et al. |
| 2010/0003391 A1 | 1/2010 | Melnyczuk |
| 2010/0035014 A1 | 2/2010 | Hammons |
| 2010/0110826 A1 | 5/2010 | D |
| 2010/0126366 A1 | 5/2010 | Kasper et al. |
| 2010/0162888 A1 | 7/2010 | Bluecher et al. |
| 2010/0202248 A1 | 8/2010 | Hirschberg et al. |
| 2010/0228209 A1 | 9/2010 | Carlucci et al. |
| 2010/0247844 A1 | 9/2010 | Curro |
| 2010/0262104 A1 | 10/2010 | Carlucci et al. |
| 2010/0280479 A1 | 11/2010 | Lindqvist et al. |
| 2010/0307665 A1 | 12/2010 | Mccutchen |
| 2010/0310837 A1 | 12/2010 | Bond et al. |
| 2011/0070423 A1 | 3/2011 | Jayakody et al. |
| 2011/0080801 A1 | 4/2011 | Georg et al. |
| 2011/0092936 A1 | 4/2011 | Kunimoto |
| 2011/0114245 A1 | 5/2011 | Nhan et al. |
| 2011/0128814 A1 | 6/2011 | Hanada |
| 2011/0150703 A1 | 6/2011 | Castro et al. |
| 2011/0174430 A1 | 7/2011 | Zhao et al. |
| 2011/0176965 A1 | 7/2011 | Castro et al. |
| 2011/0196330 A1 | 8/2011 | Hammons |
| 2011/0305104 A1 | 12/2011 | Mcguire et al. |
| 2011/0310697 A1 | 12/2011 | Hirschberg |
| 2011/0313384 A1 | 12/2011 | Akiyama |
| 2012/0001122 A1 | 1/2012 | Wattebled et al. |
| 2012/0077992 A1 | 3/2012 | Hutter et al. |
| 2012/0101460 A1 | 4/2012 | Ehmke et al. |
| 2012/0106290 A1 | 5/2012 | Meijer et al. |
| 2012/0108692 A1 | 5/2012 | Dyer |
| 2012/0134232 A1 | 5/2012 | Schneider |
| 2012/0193841 A1 | 8/2012 | Wang et al. |
| 2012/0201806 A1 | 8/2012 | Silverstein et al. |
| 2012/0209230 A1 | 8/2012 | Mansfield |
| 2012/0222567 A1 | 9/2012 | Mcneil et al. |
| 2012/0222568 A1 | 9/2012 | Byrne et al. |
| 2012/0237606 A1 | 9/2012 | Wellings |
| 2012/0296296 A1 | 11/2012 | Di Cintio et al. |
| 2012/0302440 A1 | 11/2012 | Theliander et al. |
| 2012/0308780 A1 | 12/2012 | Rottger et al. |
| 2012/0316523 A1 | 12/2012 | Hippe |
| 2012/0323201 A1 | 12/2012 | Bissah et al. |
| 2013/0006205 A1 | 1/2013 | Mckiernan et al. |
| 2013/0018341 A1 | 1/2013 | Carlucci et al. |
| 2013/0021868 A1 | 1/2013 | Doolin et al. |
| 2013/0079741 A1 | 3/2013 | Nakashita et al. |
| 2013/0107660 A1 | 5/2013 | Pappalardo |
| 2013/0218115 A1 | 8/2013 | Katsuragawa et al. |
| 2013/0253463 A1 | 9/2013 | Mansfield |
| 2013/0324959 A1 | 12/2013 | Ashraf et al. |
| 2014/0050886 A1 | 2/2014 | Burgin et al. |
| 2014/0141970 A1 | 5/2014 | Konishi et al. |
| 2014/0228796 A1 | 8/2014 | Burvall et al. |
| 2014/0276518 A1 | 9/2014 | Varona et al. |
| 2014/0295134 A1 | 10/2014 | Wood et al. |
| 2014/0295135 A1 | 10/2014 | Thompson, Jr. et al. |
| 2014/0296817 A1 | 10/2014 | Van Malderen |
| 2014/0303582 A1 | 10/2014 | Wright et al. |
| 2014/0366293 A1 | 12/2014 | Roe |
| 2015/0080823 A1 | 3/2015 | Thompson et al. |
| 2015/0119837 A1 | 4/2015 | Thompson, Jr. et al. |
| 2015/0148769 A1 | 5/2015 | Johansson et al. |
| 2015/0179750 A1 | 6/2015 | Calafut et al. |
| 2015/0245957 A1 | 9/2015 | Hashino et al. |
| 2015/0246484 A1 | 9/2015 | Hirschberg |
| 2015/0298075 A1 | 10/2015 | Glanville |
| 2015/0313770 A1 | 11/2015 | Hubbard, Jr. et al. |
| 2015/0313771 A1 | 11/2015 | Bergstrom et al. |
| 2015/0328059 A1 | 11/2015 | Robles et al. |
| 2015/0335498 A1 | 11/2015 | Hubbard, Jr. et al. |
| 2015/0343757 A1 | 12/2015 | Byrne et al. |
| 2015/0343760 A1 | 12/2015 | Byrne et al. |
| 2015/0351976 A1* | 12/2015 | Viens ................ A61F 13/51121 604/378 |
| 2015/0374560 A1 | 12/2015 | Hubbard, Jr. |
| 2015/0374561 A1 | 12/2015 | Hubbard, Jr. et al. |
| 2015/0374876 A1 | 12/2015 | Hubbard, Jr. |
| 2016/0160900 A1 | 6/2016 | Milanowski |
| 2016/0175787 A1 | 6/2016 | Merrigan et al. |
| 2016/0287452 A1 | 10/2016 | Hubbard, Jr |
| 2016/0346805 A1 | 12/2016 | Mcneil et al. |
| 2016/0375458 A1 | 12/2016 | Mcneil et al. |
| 2017/0071795 A1* | 3/2017 | Bewick-Sonntag ........................ A61F 13/534 |
| 2017/0119587 A1 | 5/2017 | Bewick-sonntag |
| 2017/0119588 A1 | 5/2017 | Bewick-sonntag |
| 2017/0119589 A1 | 5/2017 | Bewick-sonntag |
| 2017/0119593 A1* | 5/2017 | Hubbard, Jr. ...... A61F 13/15707 |
| 2017/0119594 A1 | 5/2017 | Bewick-sonntag |
| 2017/0119595 A1 | 5/2017 | Carla |
| 2017/0119596 A1 | 5/2017 | Bewick-sonntag |
| 2017/0119597 A1* | 5/2017 | Bewick-Sonntag ........................ A61F 13/15203 |
| 2017/0119598 A1* | 5/2017 | Bewick-Sonntag ........................ A61F 13/535 |
| 2017/0252708 A1 | 9/2017 | Pappalardo |
| 2017/0319401 A1 | 11/2017 | Ludher |
| 2017/0319402 A1 | 11/2017 | Morrow |
| 2017/0319403 A1 | 11/2017 | Bewick-sonntag |
| 2017/0319404 A1 | 11/2017 | Bewick-sonntag |
| 2017/0321083 A1 | 11/2017 | Fenn et al. |
| 2017/0360618 A1 | 12/2017 | Mullane |
| 2018/0110660 A1 | 4/2018 | Bewick-Sonntag |
| 2018/0168884 A1 | 6/2018 | Hubbard, Jr. et al. |
| 2018/0169832 A1 | 6/2018 | Viens et al. |
| 2018/0228656 A1 | 8/2018 | Schneider et al. |
| 2018/0228666 A1 | 8/2018 | Trinkaus et al. |
| 2018/0228667 A1 | 8/2018 | Schneider et al. |
| 2018/0228668 A1 | 8/2018 | Schneider et al. |
| 2018/0228669 A1 | 8/2018 | Schneider et al. |
| 2018/0318150 A1 | 11/2018 | Bewick-Sonntag et al. |
| 2018/0333737 A1 | 11/2018 | Mcneil et al. |
| 2020/0268574 A1 | 8/2020 | Bewick-Sonntag et al. |

FOREIGN PATENT DOCUMENTS

| | | |
|---|---|---|
| CN | 1845715 A | 10/2006 |
| DE | 2649974 A1 | 5/1977 |
| DE | 202014002444 U1 | 4/2014 |
| EP | 0138427 | 4/1985 |
| EP | 0139951 A1 | 5/1985 |
| EP | 0278476 | 2/1988 |

(56) References Cited

FOREIGN PATENT DOCUMENTS

| | | |
|---|---|---|
| EP | 0278476 A2 | 8/1988 |
| EP | 0471114 | 2/1992 |
| EP | 0532002 A1 | 3/1993 |
| EP | 0794751 | 11/1995 |
| EP | 1061966 | 3/1999 |
| EP | 1048276 A1 | 11/2000 |
| EP | 1061966 A1 | 12/2000 |
| EP | 1267769 | 1/2003 |
| EP | 1048625 B1 | 1/2004 |
| EP | 1605881 | 1/2004 |
| EP | 1139951 | 10/2004 |
| EP | 1605881 A1 | 12/2005 |
| EP | 1358894 | 11/2013 |
| FR | 2822045 A1 | 9/2002 |
| GB | 1570485 | 7/1980 |
| GB | 2326828 | 1/1999 |
| GB | 2326828 A | 1/1999 |
| JP | S5832641 A | 2/1983 |
| JP | H02239863 A | 9/1990 |
| JP | H03241079 A | 10/1991 |
| JP | H0440948 A | 2/1992 |
| JP | 2000107216 A | 4/2000 |
| JP | 2002065741 A | 3/2002 |
| JP | 2003220660 A | 8/2003 |
| JP | 2005185559 A | 7/2005 |
| JP | 2006175076 A | 7/2006 |
| JP | 2013180171 A | 9/2013 |
| JP | 2016116714 A | 6/2016 |
| WO | 9510995 A1 | 4/1995 |
| WO | WO9611714 | 4/1996 |
| WO | 9612460 A1 | 5/1996 |
| WO | 9616624 A2 | 6/1996 |
| WO | 1996017681 | 6/1996 |
| WO | 9623466 A1 | 8/1996 |
| WO | 1998022065 | 5/1998 |
| WO | 1998022067 | 5/1998 |
| WO | 1999025393 | 5/1998 |
| WO | 1999025394 | 5/1998 |
| WO | 1998024832 | 6/1998 |
| WO | 1998025999 | 6/1998 |
| WO | 1999025745 | 5/1999 |
| WO | 1999025748 | 5/1999 |
| WO | 9926670 A1 | 6/1999 |
| WO | WO9945878 | 9/1999 |
| WO | WO9947184 | 9/1999 |
| WO | WO9955269 | 11/1999 |
| WO | 0039201 | 12/1999 |
| WO | WO0000138 | 1/2000 |
| WO | WO0000136 | 12/2000 |
| WO | WO0059438 | 12/2000 |
| WO | WO0078369 | 12/2000 |
| WO | 0124754 A1 | 4/2001 |
| WO | 0168022 A1 | 9/2001 |
| WO | WO2001068022 | 9/2001 |
| WO | 0224132 A2 | 3/2002 |
| WO | 03026707 A2 | 4/2003 |
| WO | WO2003026707 | 10/2003 |
| WO | 03092568 A1 | 11/2003 |
| WO | WO2004084784 | 10/2004 |
| WO | WO2004084785 | 10/2004 |
| WO | 2007032810 | 3/2007 |
| WO | 2007113627 A1 | 10/2007 |
| WO | 2008107846 A1 | 9/2008 |
| WO | 2010/118320 * | 10/2010 ............. A47L 13/16 |
| WO | 2011038084 * | 3/2011 ............. B32B 5/22 |
| WO | 2013/180937 * | 12/2013 ............. A61L 15/24 |
| WO | 2014205015 A1 | 12/2014 |
| WO | 2015200777 A1 | 12/2015 |

OTHER PUBLICATIONS

PCT International Search Report, PCT/US2015/029199, dated Jul. 21, 2015, 12 pages.
PCT International Search Report, PCT/US2015/032154, dated Aug. 26, 2015, 10 pages.
PCT International Search Report, PCT/US2016/060588, dated Feb. 3, 2017, 14 pages.
All Office Actions, U.S. Appl. No. 14/715,984, filed May 19, 2015.
All Office Actions, U.S. Appl. No. 15/344,198, filed Nov. 4, 2016.
All Office Actions, U.S. Appl. No. 15/344,050, filed Nov. 4, 2016.
All Office Actions, U.S. Appl. No. 15/344,090, filed Nov. 4, 2016.
All Office Actions, U.S. Appl. No. 15/344,117, filed Nov. 4, 2016.
Ail Office Actions, U.S. Appl. No. 15/344,177, filed Nov. 4, 2016.
All Office Actions, U.S. Appl. No. 15/344,239, filed Nov. 4, 2016.
All Office Actions, U.S. Appl. No. 15/344,255, filed Nov. 4, 2016.
All Office Actions, U.S. Appl. No. 15/587,545, filed May 5, 2017.
All Office Actions, U.S. Appl. No. 15/587,577, filed May 5, 2017.
All Office Actions, U.S. Appl. No. 15/587,894, filed May 5, 2017.
All Office Actions, U.S. Appl. No. 15/587,908, filed May 5, 2017.
All Office Actions, U.S. Appl. No. 15/587,876, filed May 5, 2017.
All Office Actions, U.S. Appl. No. 15/969,951, filed May 3, 2018.
Estes, W. et al., "Estimation of Dissolution Rate fromin-Vivo Studies of Synthetic Fibers," Inhalation Toxicology, vol. 12. No. 11, pp. 1037-1054.
Fowkes, Determination Of Interfacial Tensions, Contact Angles, And Dispersion Farces In Surf Aces By Assuming Additivity Ofintermolecular Interactions in Surf Aces, Communications to theEditor, vol. 66, p. 382.
Fowkes, Attractive Forces at Interfaces, The interface Symposium-5, Industrial and Engineering Chemistry, vol. 58, No. 12, Dec. 1964, pp. 40-52.
Grate, J.W. et al., "Correlation of Oil-Water and Air-Water Contact Angles of Diverse Sianized Surfaces and Relationship to Fluid Interfacial Tensions", vol. 28, https://pubs.acs.org/sharing-guidelines, 2012, pp. 7182-7188.
Lepine, O. et al., "Preparation of Macrocellular PU-PS Interpenetrating Networks", Polymer, Elsevier Science Publishers B.V., GB, vol. 46, No. 23, Nov. 14, 2005, pp. 9653-9663.
Merriam Webster, "Definition of Enrobe" 2020, 5 pages.
Merriam Webster, "Definition of Planar", 2020, 7 pages.
Somos, "NanoTool Product Data Sheet", 2012, 2 pages.
Somos, "Somos Nano tool Now Commercially Available—Autocentral.com", https://www.autocentral.com/doc/somos-nanotool-now-commercially-available-0001, 2006, 2 pages.
Somos, Somos NanoTool Now Commercially Available, https://www.digitalengineering247.com/articie/somos-nanotool-now-commercially-available; Digital Engineering, Dec. 18, 2006, 4 pages.
Somos, "NanoTool MSDS Data Sheet", 2016, 5 pages.
Surface Energy Data for PTFE: Polytetrafluoroethylene, CAS # 9002-84-0, ©2009, Diversified Enterprises, 3 pages.
Vaezi, M. et al., "A review on 3D micro-additive manufacturing technologies", Int J Adv Manufacturing Technology, vol. 67, 2013, pp. 1721-1754.

* cited by examiner

ABSORBENT ARTICLE WITH ABSORBENT STRUCTURE HAVING ANISOTROPIC RIGIDITY

FIELD OF THE INVENTION

The present invention relates to absorbent structures useful in absorbent articles such as diapers, incontinent briefs, training pants, diaper holders and liners, sanitary hygiene garments, and the like. Specifically, the present invention relates to an absorbent structure that exhibits desirable consumer properties.

BACKGROUND OF THE INVENTION

Historically absorbent articles produced to capture urine and/or menses while being worn on the body—require the product to be over-designed structurally to maintain comfort and ensure protective product integrity after being wetted. If sufficient structural re-enforcement is not designed and implemented into these protective products, typically suffer from rapid degradation of the beneficial structural properties that are required to perform during a product wear/life-cycle. The inherent dry/wet comfort-protection trade-off has not been solved by main line product offerings within the absorbent article fields.

Therefore there exists a need to create a product that exhibits the desirable comfort level when dry and also when wet.

SUMMARY OF THE INVENTION

An Absorbent article comprising a topsheet, a backsheet, and an absorbent core comprising an absorbent structure is disclosed. The absorbent structure exhibits a Cross Direction bending rigidity between 0.3 gf*cm^2/cm and 1.6 gf*cm^2/cm and a Machine Direction bending rigidity between 1.5 gf*cm^2/cm and 14 gf*cm^2/cm.

An Absorbent article comprising a topsheet, a backsheet, and an absorbent core comprising an absorbent structure is further disclosed. The absorbent structure exhibits a Machine Direction bending rigidity to Cross Direction bending rigidity ratio of between 2 to 25.

Further disclosed is an Absorbent article comprising a topsheet, a backsheet, and an absorbent core comprising an absorbent structure. The absorbent structure exhibits a Cross Direction bending rigidity between 0.3 gf*cm^2/cm and 1.6 gf*cm^2/cm and a Machine Direction bending rigidity between 1.5 gf*cm^2/cm and 14 gf*cm^2/cm. The absorbent structure comprises a heterogeneous mass composite comprising enrobeable elements and open cell foam.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
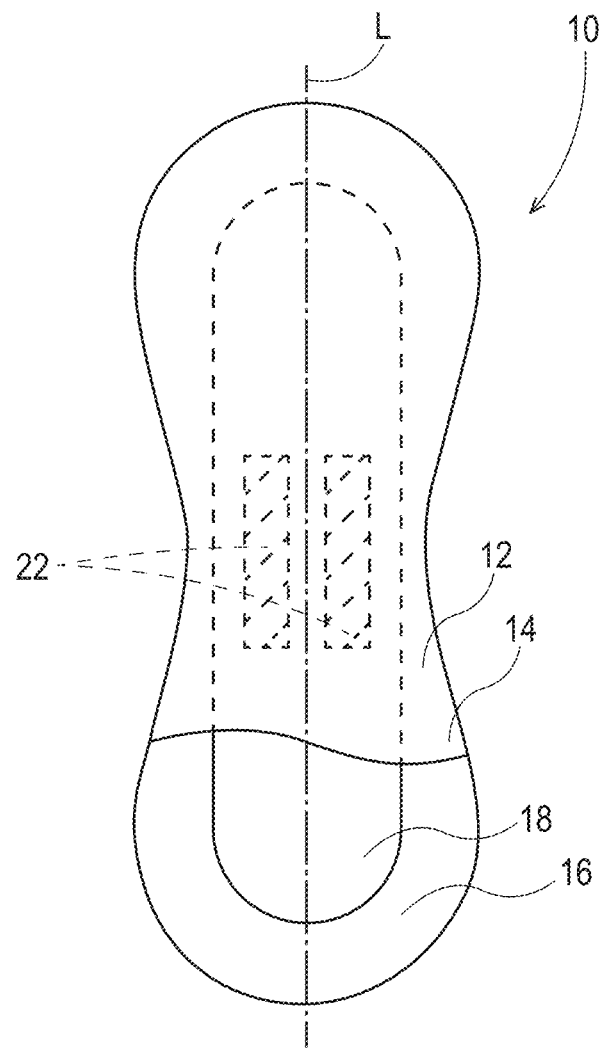
FIG. 1 is a top view of a representative catamenial device having a topsheet, backsheet, and an absorbent core.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

In the following description the term "cellulose fibers" is used. Cellulose fibers comprise naturally occurring fibers based on cellulose, such as, for example cotton, linen, etc. Wood pulp fibers are one example of cellulose fibers according to the present invention. Man-made fibers derived from cellulose, such as regenerated cellulose, e.g. viscose or partially or fully acetylated cellulose derivatives (e.g. cellulose acetate or triacetate), are also considered as cellulose fibers according to the present invention.

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin, a panty liner, an adult incontinence product, a diaper, or any other product designed to absorb a bodily exudate. The absorbent structure of the present invention will be herein described in the context of a typical absorbent article, such as, for example, a sanitary napkin. Typically, such articles may comprise a liquid pervious topsheet, a backsheet and an absorbent core intermediate the topsheet and the backsheet.

As used herein, the term "bending rigidity" refers to a measurement that is quantified in grams(force in ^2/cm).

As used herein, the term "Cross Direction" or CD refers to length along the transverse axis of the absorbent article.

As used herein, an "enrobeable element" refers to an element that may be enrobed by the foam. The enrobeable element may be, for example, a fiber, a group of fibers, a tuft, or a section of a film between two apertures. It is understood that other elements are contemplated by the present invention.

A "fiber" as used herein, refers to any material that may be part of a fibrous structure. Fibers may be natural or synthetic. Fibers may be absorbent or non-absorbent.

A "fibrous structure" as used herein, refers to materials which may be broken into one or more fibers. A fibrous structure can be absorbent or adsorbent. A fibrous structure may exhibit capillary action as well as porosity and permeability.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter. Thereafter, the meltblown fibers are carried by the high velocity gas stream and are deposited on a collecting surface, often while still tacky, to form a web of randomly dispersed meltblown fibers.

As used herein, "Machine Direction" or MD refers to a length along the longitudinal axis of the absorbent article.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "non-round fibers" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, electro-spinning, meltblowing processes, spunbonding processes, spunlacing processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size may also be expressed in denier, which is a unit of weight per length of fiber. The basis weight of laminate webs suitable for use in an article of the present invention may range from about 10 gsm to about 100 gsm, depending on the ultimate use of the web.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "recovery energy" relates to an indicator of how well an absorbent structure or absorbent product may retain or regain is original shape. More specifically, "recovery energy" is a measure of the amount of work the absorbent structure or the absorbent product will perform against the consumer's body and/or garment following compression. Without being bound by theory, the upper limit for recovery energy should be the compressive energy i.e. a fully recovered product when removed from the consumer's body/garment. Dry recovery energy for between 1 and 20 cycles should be less than 250% the dry compressive energy of a new product.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample size of at least 10 fibers) larger than 7 microns, and more particularly, between about 10 and 40 microns.

As used herein, a "strata" or "stratum" relates to one or more layers wherein the components within the stratum are intimately combined without the necessity of an adhesive, pressure bonds, heat welds, a combination of pressure and heat bonding, hydro-entangling, needlepunching, ultrasonic bonding, or similar methods of bonding known in the art such that individual components may not be wholly separated from the stratum without affecting the physical structure of the other components. The skilled artisan should understand that while separate bonding is unnecessary between the strata, bonding techniques could be employed to provide additional integrity depending on the intended use.

As used herein, a "tuft" or chad relates to discrete integral extensions of the fibers of a nonwoven web. Each tuft may comprise a plurality of looped, aligned fibers extending outwardly from the surface of the web. Each tuft may comprise a plurality of non-looped fibers that extend outwardly from the surface of the web. Each tuft may comprise a plurality of fibers which are integral extensions of the fibers of two or more integrated nonwoven webs.

As used herein, a "usage cycle" relates to the duration of use of the absorbent structure as it transitions from a dry state to a saturated wet state.

While particular embodiments of the present invention have been illustrated and described, it would be obvious to those skilled in the art that various other changes and modifications may be made without departing from the spirit and scope of the invention.

GENERAL SUMMARY

The present invention relates to an absorbent structure that is flexible and maintains its resiliency while in use. The absorbent structure is a single stratum that breaks the traditional comfort-protection trade-off. The absorbent product further sustains the improved comfort throughout a wear-cycle. The comfort-protection trade-off is broken by creating a stratum that comprises both enrobeable elements and open-cell foam which is placed in or onto the enrobeable elements to create a heterogeneous mass. By selectively placing the open-cell foam into or onto the structure, the absorbent structure may be enabled to exhibit structural properties (thinness, flexibility and thru-thickness compliance) that provide the consumer with a wearing experience (dry or wet) nearly equivalent to only wearing an undergarment or panty.

The absorbent structure single stratum may comprise one or more absorbent layers. The absorbent structure single stratum may be a heterogeneous mass.

The absorbent structure may be a heterogeneous mass. The heterogeneous mass has a depth, a width, and a height. The absorbent structure may be used as any part of an absorbent article including, for example, a part of an absorbent core, as an absorbent core, and/or as a topsheet for absorbent articles such as sanitary napkins, body applied products or panty applied products, panty liners, tampons, interlabial devices, wound dressings, diapers, adult incontinence articles, and the like, which are intended for the absorption of body fluids, such as menses or blood or vaginal discharges or urine. The absorbent structure may be used in any product utilized to absorb and retain a fluid including surface wipes. The absorbent structure may be used as a paper towel. Exemplary absorbent articles in the context of the present invention are disposable absorbent articles.

The absorbent structures single stratum may be a heterogeneous mass comprising enrobeable elements and one or more portions of foam pieces. The discrete portions of foam pieces are open-celled foam.

In an embodiment, different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

The absorbent structure single stratum may be an absorbent core for an absorbent article wherein the absorbent core comprises a heterogeneous mass comprising fibers and one or more discrete portions of foam that are immobilized in the heterogeneous mass or may be combined with other layers to form an absorbent core. Other layers may contain liquid absorbent materials suitable for use in an absorbent core. Nonlimiting examples of liquid-absorbent materials suitable for use in or as a layer of an absorbent core may include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof, as is well known in the art of making catamenial products such as sanitary napkins, pantiliners, incontinence pads, and the like.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The present invention relates to an absorbent structure single stratum that contains one or more discrete open-cell foam pieces foams that are integrated into a heterogeneous mass comprising one or more enrobeable elements integrated into the one or more open-cell foams such that the two may be intertwined.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass may have void space found between the enrobeable elements, between the enrobeable elements and the enrobed elements, and between enrobed elements. The void space may contain a gas such as air. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the, such as for example, between 20 g/g and 190 g/g of the heterogeneous mass, such as, for example 30 g/g, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces may be intertwined within the heterogeneous mass. The open-cell foam pieces may be intertwined throughout the heterogeneous mass. The open-cell foam pieces may be intertwined within a portion of the heterogeneous mass. The open-cell foam pieces may be intertwined within the heterogeneous mass such that the open-cell foam enrobes one or more of the enrobeable elements such as, for example, fibers within the mass. The open-cell foam may be polymerized around the enrobeable elements.

A discrete open-cell foam piece may enrobe more than one enrobeable element. The enrobeable elements may be enrobed together as a bunch. Alternatively, more than one enrobeable element may be enrobed by the discrete open-cell foam piece without contacting another enrobeable element.

The open-cell foam pieces may be discrete. Open-cell foam pieces are considered discrete in that they are not continuous throughout the entire heterogeneous mass. Not continuous throughout the entire heterogeneous mass represents that at any given point in the heterogeneous mass, the open-cell absorbent foam is not continuous in at least one of the cross sections of a longitudinal, a vertical, and a lateral plane of the heterogeneous mass. The absorbent foam may or may not be continuous in the lateral and the vertical planes of the cross section for a given point in the heterogeneous mass. The absorbent foam may or may not be continuous in the longitudinal and the vertical planes of the cross section for a given point in the heterogeneous mass. The absorbent foam may or may not be continuous in the longitudinal and the lateral planes of the cross section for a given point in the heterogeneous mass.

When the open-cell foam is not continuous in at least one of the cross sections of the longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. A foam piece may be surrounded by the elements that make up the enrobeable elements. A foam piece may be located on the outer perimeter of the heterogeneous mass such that only a portion of the foam piece is entangled with the elements of the heterogeneous mass.

The open-cell foam pieces may expand upon being contacted by a fluid to form a channel of discrete open-cell foam pieces. The open-cell foam pieces may or may not be in contact prior to being expanded by a fluid.

An open-celled foam may be integrated onto the enrobeable elements prior to being polymerized. The open-cell foam pieces may be partially polymerized prior to being impregnated into or onto the enrobeable elements such that they become intertwined. After being impregnated into or onto the enrobeable elements, the open-celled foam in either a liquid or solid state are polymerized to form one or more open-cell foam pieces. The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

The open cell foam pieces may be impregnated prior to polymerization into or onto two or more different enrobeable elements that are combined to create a heterogeneous mixture of enrobeable elements. The two or more different enrobeable elements may be intertwined such that one enrobeable element may be surrounded by multiples of the second enrobeable element, such as, for example by using more than one type of fiber in a mixture of fibers or by coating one or more fibers with surfactant. The two or more different enrobeable elements may be layered within the heterogeneous mass along any of the vertical, longitudinal, and/or lateral planes such that the enrobeable elements are profiled within the heterogeneous mass for an enrobeable element inherent property or physical property, such as, for example, hydrophobicity, fiber diameter, fiber or composition. It is understood that any inherent property or physical property of the enrobeable elements listed is contemplated herein.

Dependent upon the desired foam density, polymer composition, specific surface area, or pore-size (also referred to as cell size), the open-celled foam may be made with different chemical composition, physical properties, or both. For instance, dependent upon the chemical composition, an open-celled foam may have a density of 0.0010 g/cc to about 0.25 g/cc, or from 0.002 g/cc to about 0.2 g/cc, or from about 0.005 g/cc to about 0.15 g/cc, or from about 0.01 g/cc to about 0.1 g/cc, or from about 0.02 g/cc to about 0.08 g/cc, or about 0.04 g/cc.

Open-cell foam pore-sizes may range in average diameter of from 1 to 800 μm, such as, for example, between 2 and 100 μm, between 2-50 μm, between 50 and 700 μm, between 100 and 600 μm, between 200 and 500 μm, between 300 and 400 μm.

The foam pieces may have a relatively uniform cell size. For example, the average cell size on one major surface may be about the same or vary by no greater than 10% as compared to the opposing major surface. The average cell size of one major surface of the foam may differ from the opposing surface. For example, in the foaming of a thermosetting material it is not uncommon for a portion of the cells at the bottom of the cell structure to collapse resulting in a lower average cell size on one surface. The cell size may be determined based upon the method found below.

The foams produced from the present invention are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1 μm in average diameter size are in fluid communication with at least one adjoining cell.

In addition to being open-celled, the foams may be sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

For example when used in certain absorbent articles, an open-cell foam may be flexible and exhibit an appropriate glass transition temperature (Tg). The Tg represents the midpoint of the transition between the glassy and rubbery states of the polymer.

The Tg of a region may be less than about 200° C. for foams used at about ambient temperature conditions, or less than about 90° C. The Tg may be less than 50° C.

The open-cell foam pieces may be distributed in any suitable manner throughout the heterogeneous mass. The open-cell foam pieces may be profiled along the vertical axis such that smaller pieces are located above larger pieces. Alternatively, the pieces may be profiled such that smaller pieces are below larger pieces. The open-cell pieces may be profiled along a vertical axis such that they alternate in size along the axis.

The open-cell foam pieces may be profiled along the longitudinal axis such that smaller pieces are located in front of larger pieces. Alternatively, the pieces may be profiled such that smaller pieces are behind larger pieces. The open-cell pieces may be profiled along a longitudinal axis such that they alternate in size along the axis.

The open-cell foam pieces may be profiled along the lateral axis such the size of the pieces goes from small to large or from large to small along the lateral axis. Alternatively, the open-cell pieces may be profiled along a lateral axis such that they alternate in size along the axis.

The open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

The open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics. The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. The open-cell foam pieces may be distributed in a manner that forms a design or shape when viewed from a top planar view. The open-cell foam pieces may be distributed in a manner that forms stripes, ellipticals, squares, or any other known shape or pattern.

The distribution may be optimized dependent on the intended use of the heterogeneous mass. For example, a different distribution may be chosen for the absorption of aqueous fluids such as urine when used in a diaper or water when used in a paper towel versus for the absorption of a proteinaceous fluid such as menses. Further, the distribution may be optimized for uses such as dosing an active or to use the foam as a reinforcing element.

Different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

The foam pieces may be similar in composition yet exhibit different properties. For example, using HIPE foam, some foam pieces may be thin until wet while others may have been expanded within the heterogeneous mass.

The foam pieces and enrobeable elements may be selected to complement each other. For example, a foam that exhibits high permeability with low capillarity may enrobe an element that exhibits high capillarity to wick the fluid through the heterogeneous mass. It is understood that other combinations may be possible wherein the foam pieces complement each other or wherein the foam pieces and enrobeable elements both exhibit similar properties.

Profiling may occur using more than one heterogeneous mass with each heterogeneous mass having one or more types of foam pieces. The plurality of heterogeneous masses may be layered so that the foam is profiled along any one of the longitudinal, lateral, or vertical axis based on one or more characteristics of the open-cell foam pieces for an overall product that contains the plurality of heterogeneous masses. Further, each heterogeneous mass may have a different enrobeable element to which the foam is attached. For example, a first heterogeneous mass may have foam particles enrobing a nonwoven while a second heterogeneous mass adjacent the first heterogeneous mass may have foam particles enrobing a film or one surface of a film.

In an embodiment, the open cell foam may be made from a polymer formula that can include any suitable thermoplastic polymer, or blend of thermoplastic polymers, or blend of thermoplastic and non-thermoplastic polymers.

Examples of polymers, or base resins, suitable for use in the foam polymer formula include styrene polymers, such as polystyrene or polystyrene copolymers or other alkenyl aromatic polymers; polyolefins including homo or copolymers of olefins, such as polyethylene, polypropylene, polybutylene, etc.; polyesters, such as polyalkylene terephthalate; and combinations thereof. A commercially available example of polystyrene resin is Dow STYRON® 685D, available from Dow Chemical Company in Midland, Mich., U.S.A.

Coagents and compatibilizers can be utilized for blending such resins. Crosslinking agents can also be employed to enhance mechanical properties, foamability and expansion. Crosslinking may be done by several means including electron beams or by chemical crosslinking agents including organic peroxides. Use of polymer side groups, incorporation of chains within the polymer structure to prevent polymer crystallization, lowering of the glass transition temperature, lowering a given polymer's molecular weight distribution, adjusting melt flow strength and viscous elastic properties including elongational viscosity of the polymer melt, block copolymerization, blending polymers, and use of polyolefin homopolymers and copolymers have all been used to improve foam flexibility and foamability. Homopolymers can be engineered with elastic and crystalline areas. Syndiotactic, atactic and isotactic polypropylenes, blends of such and other polymers can also be utilized. Suitable polyolefin resins include low, including linear low, medium and high-density polyethylene and polypropylene, which are normally made using Ziegler-Natta or Phillips catalysts and are relatively linear; generally more foamable are resins having branched polymer chains. Isotactic propylene homopolymers and blends are made using metallocene-based catalysts. Olefin elastomers are included.

Ethylene and α-olefin copolymers, made using either Ziegler-Natta or a metallocene catalyst, can produce soft, flexible foam having extensibility. Polyethylene crosslinked with α-olefins and various ethylene ionomer resins can also be utilized. Use of ethyl-vinyl acetate copolymers with other polyolefin-type resins can produce soft foam. Common modifiers for various polymers can also be reacted with chain groups to obtain suitable functionality. Suitable alkenyl aromatic polymers include alkenyl aromatic homopolymers and copolymers of alkenyl aromatic compounds and copolymerizable ethylenically unsaturated comonomers including minor proportions of non-alkenyl aromatic polymers and blends of such. Ionomer resins can also be utilized.

Other polymers that may be employed include natural and synthetic organic polymers including cellulosic polymers, methyl cellulose, polylactic acids, polyvinyl acids, polyacrylates, polycarbonates, starch-based polymers, polyetherimides, polyamides, polyesters, polymethylmethacrylates, and copolymer/polymer blends. Rubber-modified polymers such as styrene elastomers, styrene/butadiene copolymers, ethylene elastomers, butadiene, and polybutylene resins, ethylene-propylene rubbers, EPDM, EPM, and other rubbery homopolymers and copolymers of such can be added to enhance softness and hand. Olefin elastomers can also be utilized for such purposes. Rubbers, including natural rubber, SBR, polybutadiene, ethylene propylene terpolymers, and vulcanized rubbers, including TPVs, can also be added to improve rubber-like elasticity.

Thermoplastic foam absorbency can be enhanced by foaming with spontaneous hydrogels, commonly known as superabsorbents. Superabsorbents can include alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile grafted starch, acrylic acid grafted starch, carboxy-methylcellulose, isobutylene maleic anhydride copolymers, and mixtures thereof. Further suitable polymers include inorganic polymers, such as polyphosphazene, and the like. Furthermore, thermoplastic foam biodegradability and absorbency can be enhanced by foaming with cellulose-based and starch-based components such as wood and/or vegetable fibrous pulp/flour.

In addition to any of these polymers, the foam polymer formula may also, or alternatively, include diblock, triblock, tetrablock, or other multi-block thermoplastic elastomeric and/or flexible copolymers such as polyolefin-based thermoplastic elastomers including random block copolymers including ethylene α-olefin copolymers; block copolymers including hydrogenated butadiene-isoprene-butadiene block copolymers; stereoblock polypropylenes; graft copolymers, including ethylene-propylene-diene terpolymer or ethylene-propylene-diene monomer (EPDM), ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SIBS), styrene-ethylene/butylene-styrene (SEBS), or styrene-ethylene/propylene-styrene (SEPS), which may be obtained from Kraton Polymers of Belpre, Ohio, U.S.A., under the trade designation KRATON® elastomeric resin or from Dexco, a division of ExxonMobil Chemical Company in Houston, Tex., U.S.A., under the trade designation VECTOR® (SIS and SBS polymers) or SEBS polymers as the SEPTON® series of thermoplastic rubbers from Kuraray America, Inc. in New York, N.Y., U.S.A.; blends of thermoplastic elastomers with dynamic vulcanized elastomer-thermoplastic blends; thermoplastic polyether ester elastomers; ionomeric thermoplastic elastomers; thermoplastic elastic polyurethanes, including those available from E.I. Du Pont de Nemours in Wilmington, Del., U.S.A., under the trade name LYCRA® polyurethane, and ESTANE® available from Noveon, Inc. in Cleveland, Ohio, U.S.A.; thermoplastic elastic polyamides, including polyether block amides available from ATOFINA Chemicals, Inc. in Philadelphia, Pa., U.S.A., under the trade name PEBAX® polyether block amide; thermoplastic elastic polyesters, including those available from E.I. Du Pont de Nemours Company, under the trade name HYTREL®, and ARNITEL® from DSM Engineering Plastics of Evansville, Ind., U.S.A., and single-site or metallocene-catalyzed polyolefins having a density of less than about 0.89 grams/cubic centimeter such as metallocene polyethylene resins, available from Dow Chemical Company in Midland, Mich., U.S.A. under the trade name AFFINITY™; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS, and SEPS. In these copolymers the A blocks are polystyrene and the B blocks are the rubbery component. Generally these triblock copolymers have molecular weights that can vary from the low thousands to hundreds of thousands and the styrene content can range from 5% to 75% based on the weight of the triblock copolymer. A diblock copolymer is similar to the triblock but is of an AB structure. Suitable diblocks include styrene-isoprene diblocks, which have a molecular weight of approximately one-half of the triblock molecular weight and having the same ratio of A blocks to B blocks. Diblocks with a different ratio of A to B blocks or a molecular weight larger or greater than one-half of triblock copolymers may be suitable for improving the foam polymer formula for producing low-density, soft, flexible, absorbent foam via polymer extrusion.

Suitably, the foam polymer formula includes up to about 90%, by weight, of polystyrene, and at least 10%, by weight, of thermoplastic elastomer. More particularly, the foam polymer formula may include between about 45% and about 90%, by weight, of polystyrene, and between about 10% and about 55%, by weight, of thermoplastic elastomer. Alternatively, the foam polymer formula may include between about 50% and about 80%, by weight, of polystyrene, and between about 20% and about 50%, by weight, of thermoplastic elastomer. In one embodiment, for example, the foam polymer formula may include equal amounts of polystyrene and thermoplastic elastomer.

In another embodiment, the foam polymer formula may include about 40% to about 80% by weight polystyrene and about 20% to about 60% by weight thermoplastic elastomer. In another embodiment, the foam polymer formula may include about 50% to about 70% by weight polystyrene and about 30% to about 50% by weight thermoplastic elastomer.

In accordance with the embodiment, a plasticizing agent can be included in the foam polymer formula. A plasticizing agent is a chemical agent that imparts flexibility, stretchability and workability. The type of plasticizing agent has an influence on foam gel properties, blowing agent migration resistance, cellular structure, including the fine cell size, and number of open cells. Typically plasticizing agents are of low molecular weight. The increase in polymer chain mobility and free volume caused by incorporation of a plasticizing agent typically results in a Tg decrease, and plasticizing agent effectiveness is often characterized by this measurement. Petroleum-based oils, fatty acids, and esters are commonly used and act as external plasticizing agents or solvents because they do not chemically bond to the polymer yet remain intact in the polymer matrix upon crystallization.

The plasticizing agent increases cell connectivity by thinning membranes between cells to the point of creating porous connections between cells; thus, the plasticizing agent increases open-cell content. Suitably, the plasticizing agent is included in an amount between about 0.5% and about 10%, or between about 1% and about 10%, by weight, of the foam polymer formula. The plasticizing agent is gradually and carefully metered in increasing concentration into the foam polymer formula during the foaming process because too much plasticizing agent added at once creates cellular instability, resulting in cellular collapse.

Examples of suitable plasticizing agents include polyethylene, ethylene vinyl acetate, mineral oil, palm oil, waxes, esters based on alcohols and organic acids, naphthalene oil, paraffin oil, and combinations thereof. A commercially available example of a suitable plasticizing agent is a small-chain polyethylene that is produced as a catalytic polymerization of ethylene; because of its low molecular weight it is often referred to as a "wax." This low-density, highly branched polyethylene "wax" is available from Eastman Chemical Company of Kingsport, Tenn., U.S.A., under the trade designation EPOLENE® C-10.

In order for the foam to be used in personal care and medical product applications and many absorbent wiping articles and non-personal care articles, the foam must meet stringent chemical and safety guidelines. A number of plasticizing agents are FDA-approved for use in packaging materials. These plasticizing agents include: acetyl tributyl citrate; acetyl triethyl citrate; p-tert-butylphenyl salicylate; butyl stearate; butylphthalyl butyl glycolate; dibutyl sebacate; di-(2-ethylhexyl) phthalate; diethyl phthalate; diisobutyl adipate; diisooctyl phthalate; diphenyl-2-ethylhexyl phosphate; epoxidized soybean oil; ethylphthalyl ethyl glycolate; glycerol monooleate; monoisopropyl citrate; mono-, di-, and tristearyl citrate; triacetin (glycerol triacetate); triethyl citrate; and 3-(2-xenoyl)-1,2-epoxypropane.

In certain embodiments, the same material used as the thermoplastic elastomer may also be used as the plasticizing agent. For example, the KRATON® polymers, described above, may be used as a thermoplastic elastomer and/or a plasticizing agent. In which case, the foam polymer formula may include between about 10% and about 50%, by weight, of a single composition that acts as both a thermoplastic elastomer and a plasticizing agent. Described in an alternative manner, the foam may be formed without a plasticizing agent per se; in which case, the foam polymer formula may include between about 10% and about 50%, by weight, of the thermoplastic elastomer.

Foaming of soft, flexible polymers, such as thermoplastic elastomers, to a low density is difficult to achieve. The addition of a plasticizing agent makes foaming to low densities even more difficult to achieve. The method of the invention overcomes this difficulty through the inclusion of a surfactant in the foam polymer formula. The surfactant stabilizes the cells, thereby counteracting cellular collapse while retaining an open-cell structure. This stabilization of the cells creates cell uniformity and control of cell structure. In addition to enabling foaming of plasticized thermoplastic elastomer polymer containing foam formulations to low densities, the surfactant also provides wettability to enable the resulting foam to absorb fluid.

The foam pieces may be made from a thermoplastic absorbent foam such as a polyurethane foam. The thermoplastic foam may comprise surfactant and plasticizing agent. Polyurethane polymers are generally formed by the reaction of at least one polyisocyanate component and at least one polyol component. The polyisocyanate component may comprise one or more polyisocyanates. The polyol component may comprise one or more polyols. The concentration of a polyol may be expressed with regard to the total polyol component. The concentration of polyol or polyisocyanate may alternatively be expressed with regard to the total polyurethane concentration. Various aliphatic and aromatic polyisocyanates have been described in the art. The polyisocyanate utilized for forming the polyurethane foam typically has a functionality between from 2 and 3. In some embodiments, the functionality is no greater than about 2.5.

In one embodiment, the foam is prepared from at least one aromatic polyisocyanate. Examples of aromatic polyisocyanates include those having a single aromatic ring such as are toluene 2,4 and 2,6-diisocyanate (TDI) and naphthalene 1,5-diisocyanate; as well as those having at least two aromatic rings such as diphenylmethane 4,4'-, 2,4'- and 2,2'-diisocyanate (MDI).

In favored embodiments, the foam is prepared from one or more (e.g. aromatic) polymeric polyisocyanates. Polymeric polyisocyanates typically have a (weight average) molecular weight greater than a monomeric polyisocyanate (lacking repeating units), yet lower than a polyurethane prepolymer. Thus, the polyurethane foam is derived from at least one polymeric polyisocyanate that lacks urethane linkages. In other words, the polyurethane foam is derived from a polymeric isocyanate that is not a polyurethane prepolymer. Polymeric polyisocyanates comprises other linking groups between repeat units, such as isocyanurate groups, biuret groups, carbodiimide groups, uretonimine groups, uretdione groups, etc. as known in the art.

Some polymeric polyisocyanates may be referred to as "modified monomeric isocyanate". For example pure 4,4'-methylene diphenyl diisocyanate (MDI) is a solid having a melting point of 38° C. and an equivalent weight of 125 g/equivalent. However, modified MDIs, are liquid at 38° C. and have a higher equivalent weight (e.g. 143 g/equivalent). The difference in melting point and equivalent weight is believed to be a result of a small degree of polymerization, such as by the inclusion of linking groups, as described above.

Polymeric polyisocyanates, including modified monomeric isocyanate, may comprise a mixture of monomer in combination with polymeric species inclusive of oligomeric species. For example, polymeric MDI is reported to contain 25-80% monomeric 4,4'-methylene diphenyl diisocyanate as well as oligomers containing 3-6 rings and other minor isomers, such as 2,2' isomer.

Polymeric polyisocyanates typically have a low viscosity as compared to prepolymers. The polymeric isocyanates utilized herein typically have a viscosity no greater than about 300 cps at 25° C. and in some embodiments no greater than 200 cps or 100 cps at 25° C. The viscosity is typically at least about 10, 15, 20 or 25 cps at 25° C.

The equivalent weight of polymeric polyisocyanates is also typically lower than that of prepolymers. The polymeric isocyanates utilized herein typically have an equivalent weight of no greater than about 250 g/equivalent and in some embodiments no greater than 200 g/equivalent or 175 g/equivalent. In some embodiments, the equivalent weight is at least 130 g/equivalent.

The average molecular weight (Mw) of polymeric polyisocyanates is also typically lower than that of polyurethane prepolymers. The polymeric isocyanates utilized herein typically have an average molecular weight (Mw) of no greater than about 500 Da and in some embodiments no greater than 450, 400, or 350 Da. In some embodiments, the polyurethane is derived from a single polymeric isocyanate or a blend of polymeric isocyanates. Thus, 100% of the isocyanate component is polymeric isocyanate(s). In other embodiments, a major portion of the isocyanate component is a single polymeric isocyanate or a blend of polymeric isocyanates. In these embodiments, at least 50, 60, 70, 75, 80, 85 or 90 wt-% of the isocyanate component is polymeric isocyanate(s).

Some illustrative polyisocyanates include for example, polymeric MDI diisocyanate from Huntsman Chemical Company, The Woodlands, Tex., under the trade designation "RUBINATE 1245"; and modified MDI isocyanate available from Huntsman Chemical Company under the trade designation "SUPRASEC 9561".

The aforementioned isocyanates are reacted with a polyol to prepare the polyurethane foam material. The polyurethane foams are hydrophilic, such that the foam absorbs aqueous liquids, particularly body fluids. The hydrophilicity of the polyurethane foams is typically provided by use of an isocyanate-reactive component, such as a polyether polyol, having a high ethylene oxide content.

Examples of useful polyols include adducts [e.g., polyethylene oxide, polypropylene oxide, and poly(ethylene oxide-propylene oxide) copolymer] of dihydric or trihydric alcohols (e.g., ethylene glycol, propylene glycol, glycerol, hexanetriol, and triethanolamine) and alkylene oxides (e.g., ethylene oxide, propylene oxide, and butylene oxide). Polyols having a high ethylene oxide content can also be made by other techniques as known in the art. Suitable polyols typically have a molecular weight (Mw) of 100 to 5,000 Da and contain an average functionality of 2 to 3.

The polyurethane foam is typically derived from (or in other words is the reaction product of) at least one polyether polyol having ethylene oxide (e.g. repeat) units. The polyether polyol typically has an ethylene oxide content of at least 10, 15, 20 or 25 wt-% and typically no greater than 75 wt-%. Such polyether polyol has a higher functionality than the polyisocyanate. In some embodiments, the average functionality is about 3. The polyether polyol typically has a viscosity of no greater than 1000 cps at 25° C. and in some embodiments no greater than 900, 800, or 700 cps. The molecular weight of the polyether polyol is typically at least 500 or 1000 Da and in some embodiments no greater than 4000 or 3500, or 3000 Da. Such polyether polyol typically has a hydroxyl number of at least 125, 130, or 140. An illustrative polyol includes for example a polyether polyol product obtained from the Carpenter Company, Richmond, Va. under the designation "CDB-33142 POLYETHER POLYOL", "CARPOL GP-5171".

In some embodiments, one or more polyether polyols having a high ethylene oxide content and a molecular weight (Mw) of no greater than 5500, or 5000, or 4500, or 4000, or 3500, or 3000 Da, as just described, are the primary or sole polyether polyols of the polyurethane foam. For example, such polyether polyols constitute at least 50, 60, 70, 80, 90, 95 or 100 wt-% of the total polyol component. Thus, the polyurethane foam may comprise at least 25, 30, 35, 40, 45 or 50 wt-% of polymerized units derived from such polyether polyols.

In other embodiments, one or more polyether polyols having a high ethylene oxide content are utilized in combination with other polyols. In some embodiments, the other polyols constitute at least 1, 2, 3, 4, or 5 wt-% of the total polyol component. The concentration of such other polyols typically does not exceed 40, or 35, or 30, or 25, or 20, or 15, or 10 wt-% of the total polyol component, i.e. does not exceed 20 wt-%, or 17.5 wt-%, or 15 wt-%, or 12.5 wt-%, or 10 wt-%, or 7.5 wt-%, or 5 wt-% of the polyurethane. Illustrative other polyols include a polyether polyol product (Chemical Abstracts Number 25791-96-2) that can be obtained from the Carpenter Company, Richmond, Va. under the designation "CARPOL GP-700 POLYETHER POLYOL" and a polyether polyol product (Chemical Abstracts Number 9082-00-2) that can be obtained from Bayer Material Science, Pittsburgh, Va. under the trade designation "ARCOL E-434". In some embodiments, such optional other polyols may comprise polypropylene (e.g. repeat) units.

The polyurethane foam generally has an ethylene oxide content of at least 10, 1 1, or 12 wt-% and no greater than 20, 19, or 18 wt-%. In some embodiments, the polyurethane foam has an ethylene oxide content of no greater than 17 or 16 wt-%.

The kinds and amounts of polyisocyanate and polyol components are selected such that the polyurethane foam is relatively soft, yet resilient. These properties can be characterized for example by indentation force deflection and constant deflection compression set, as measured according to the test methods described in the examples. In some embodiments, the polyurethane foam has an indentation force deflection of less than 75N at 50%. The indentation force deflection at 50% may be less than 70N, or 65N, or 60 N. In some embodiments, the polyurethane foam has an indentation force deflection of less than 100N at 65%. The indentation force deflection at 65% may be less than 90N, or 80N, or 70 N, or 65N, or 60N. In some embodiments, the indentation force deflection at 50% or 65% is typically at least 30N or 35N. The constant deflection compression set at 50% deflection can be zero and is typically at least 0.5, 1 or 2% and generally no greater than 35%. In some embodiments, the constant deflection compression set at 50% deflection is no greater than 30%, or 25%, or 20%, or 15%, or 10%.

The polyurethane foam may comprise known and customary polyurethane formation catalysts such as organic tin compounds and/or an amine-type catalyst. The catalysts are preferably used in an amount of from 0.01 to 5 wt-% of the polyurethane. The amine-type catalyst is typically a tertiary amine. Examples of suitable tertiary amine include monoamines such as triethylamine, and dimethyl cyclohexylamine; diamines such as tetramethylethylenediamine, and tetramethylhexanediamine; triamines such as tetramethylguanidine; cyclic amines such as triethylenediamine, dimethylpiperadine, and methylmorphorine; alcoholamines such as dimethylaminoethanol, trimethylaminoethylethanolamine, and hydroxyethylmorphorine; ether amines such as bisdimethylaminoethyl ethanol; diazabicycloalkenes such as 1,5-diazabicyclo(5,4,0)undecene-7 (DBU), and 1,5-diazabicyclo(4,3,0)nonene-5; and organic acid salts of the diazabicycloalkenes such as phenol salt, 2-ethylhexanoate and formate of DBU. These amines can be used either singly or in combination. The amine-type catalyst can be used in an amount no greater than 4, 3, 2, 1 or 0.5 wt-% of the polyurethane.

The polyurethane typically comprises a surfactant to stabilize the foam. Various surfactants have been described in the art. In one embodiment a silicone surfactant is employed that comprises ethylene oxide (e.g. repeat) units, optionally in combination with propylene oxide (e.g. repeat) units such as commercially available from Air Products under the trade designation "DABCO DC-198". In some embodiments, the concentration of hydrophilic surfactant typically ranges from about 0.05 to 1 or 2 wt-% of the polyurethane.

The polyurethane foam may comprise various additives such as surface active substances, foam stabilizers, cell regulators, blocking agents to delay catalytic reactions, fire retardants, chain extenders, crosslinking agents, external and internal mold release agents, fillers, pigments (titanium dioxide), colorants, optical brighteners, antioxidants, stabilizers, hydrolysis inhibitors, as well as anti-fungal and anti-bacteria substances. Such other additives are typically collectively utilized at concentrations ranging from 0.05 to 10 wt-% of the polyurethane.

In some embodiments, the absorbent foam is white in color. Certain hindered amine stabilizers can contribute to discoloration, such as yellowing, of the absorbent foam. In some embodiments, the absorbent foam is free of diphenylamine stabilizer and/or phenothiazine stabilizer.

In other embodiments, the absorbent foam may be a colored (i.e. a color other than white). The white or colored absorbent foam can include a pigment in at least one of the components. In preferred embodiments, pigment is combined with a polyol carrier and is added to the polyol liquid stream during manufacture of the polyurethane foam. Commercially available pigments include for example DispersiTech™ 2226 White, DispersiTech™ 2401 Violet, DispersiTech™ 2425 Blue, DispersiTech™ 2660 Yellow, and DispersiTech™ 28000 Red from Milliken in Spartansburg, S.C. and Pdi® 34-68020 Orange from Ferro in Cleveland, Ohio.

In the production of polyurethane foams, the polyisocyanate component and polyol component are reacted such that an equivalence ratio of isocyanate groups to the sum of hydroxyl groups is no greater than 1 to 1. In some embodiments, the components are reacted such that there are excess hydroxyl groups (e.g. excess polyol). In such embodiments, the equivalence ratio of isocyanate groups to the sum of the hydroxy groups is at least 0.7 to 1. For example, the ratio may be at least 0.75:1, or at least 0.8:1.

The hydrophilic (e.g. polyol(s)) component(s) of the (e.g. polyurethane) polymeric foam provide the desired absorption capacity of the foam. Thus the foam may be free of superabsorbent polymer. Further, the polyurethane foam is free of amine or imine complexing agent such as ethylenimine, polyethylenimine, polyvinylamine, carboxy-methylated polyethylenimines, phosphono-methylated polyethylenimines, quaternized polyethylenimines and/or dithiocarbamitized polyethylenimines; as described for example in U.S. Pat. Nos. 6,852,905 and 6,855,739.

The polymeric (e.g. polyurethane) foam typically has an average basis weight of at least 100, 150, 200, or 250 gsm and typically no greater than 500 gsm. In some embodiments the average basis weight is no greater than 450, or 400 gsm. The average density of the (e.g. polyurethane) polymeric foam is typically at least 3, 3.5 or 4 lbs/ft$^3$ and no greater than 7 lbs/ft$^3$.

The open-celled foam may be a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. The aqueous phase to oil phase ratio may be between about 10:1 and about 75:1, and the aqueous phase to oil phase ratio may be between about 13:1 and about 65:1. This is termed the "water-to-oil" or W:O ratio and may be used to determine the density of the resulting polyHIPE foam. As discussed, the oil phase may contain one or more of monomers, comonomers, photoinitiators, crosslinkers, and emulsifiers, as well as optional components. The water phase may contain water and one or more components such as electrolyte, initiator, or optional components.

The open-cell foam may be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, or after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE may then be withdrawn or pumped from the mixing zone. One method for forming HIPEs using a continuous process is described in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

The emulsion may be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

Following polymerization, the resulting foam pieces are saturated with aqueous phase that needs to be removed to obtain substantially dry foam pieces. Foam pieces may be squeezed free of most of the aqueous phase by using compression, for example by running the heterogeneous mass comprising the foam pieces through one or more pairs of nip rollers. The nip rollers may be positioned such that they squeeze the aqueous phase out of the foam pieces. The nip rollers may be porous and have a vacuum applied from the inside such that they assist in drawing aqueous phase out of the foam pieces. Nip rollers may be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller may be pressurized while the other, for example the second nip roller, may be evacuated, so as to both blow and draw the aqueous phase out the of the foam. The nip rollers may also be heated to assist in removing the aqueous phase. Nip rollers may be applied to non-rigid foams, that is, foams whose walls would not be destroyed by compressing the foam pieces.

In place of or in combination with nip rollers, the aqueous phase may be removed by sending the foam pieces through a drying zone where it is heated, exposed to a vacuum, or a combination of heat and vacuum exposure. Heat may be applied, for example, by running the foam though a forced air oven, IR oven, microwave oven or radiowave oven. The extent to which a foam is dried depends on the application. Greater than 50% of the aqueous phase may be removed. Greater than 90%, and in still other embodiments greater than 95% of the aqueous phase may be removed during the drying process.

Open-cell foam may be produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include C4-C18 alkyl acrylates and C2-C18 methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams. "Toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers may be used to slow down the polymerization rate of a HIPE. Examples of monomers of this type may have styrene and vinyl chloride.

The oil phase may further contain an emulsifier used for stabilizing the HIPE. Emulsifiers used in a HIPE may include: (a) sorbitan monoesters of branched C16-C24 fatty acids; linear unsaturated C16-C22 fatty acids; and linear saturated C12-C14 fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched C16-C24 fatty acids, linear unsaturated C16-C22 fatty acids, or linear saturated C12-C14 fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched C16-C24 alcohols, linear unsaturated C16-C22 alcohols, and linear saturated C12-C14 alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they may have between about 1% and about 20%, in certain embodiments from about 2% to about 15%, and in certain other embodiments from about 3% to about 12% by weight of the oil phase. Coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain C12-C22 dialiphatic quaternary ammonium salts, short chain C1-C4 dialiphatic quaternary ammonium salts, long chain C12-C22 dialkoyl(alkenoyl)-2-hydroxyethyl, short chain C1-C4 dialiphatic quaternary ammonium salts, long chain C12-C22 dialiphatic imidazolinium quaternary ammonium salts, short chain C1-C4 dialiphatic imidazolinium quaternary ammonium salts, long chain C12-C22 monoaliphatic benzyl quaternary ammonium salts, long chain C12-C22 dialkoyl(alkenoyl)-2-aminoethyl, short chain C1-C4 monoaliphatic benzyl quaternary ammonium salts, short chain C1-C4 monohydroxyaliphatic quaternary ammonium salts. Ditallow dimethyl ammonium methyl sulfate (DTDMAMS) may be used as a coemulsifier.

The oil phase may comprise a photoinitiator at between about 0.05% and about 10%, and in certain embodiments between about 0.2% and about 10% by weight of the oil phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of about 200 nanometers (nm) to about 800 nm, in certain embodiments about 200 nm to about 350 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine] oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio) phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl) phenyl]propanone] (sold by Lamberti spa, Gallarate, Italy as ESACURE® KIP EM.

The dispersed aqueous phase of a HIPE may have water, and may also have one or more components, such as initiator, photoinitiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte may include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator may be present at up to about 20 mole percent based on the total moles of polymerizable monomers present in the oil phase. The initiator may be present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, and other suitable azo initiators. To reduce the potential for premature polymerization which may clog the emulsification system, addition of the initiator to the monomer phase may be just after or near the end of emulsification.

Photoinitiators present in the aqueous phase may be at least partially water soluble and may have between about 0.05% and about 10%, and in certain embodiments between about 0.2% and about 10% by weight of the aqueous phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane] disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzal acetone, 4,4'-dicarboxymethoxydibenzalcyclohexanone,4-dimethylamino-4'-carboxymethoxydibenzalacetone; and 4,4'-disulphoxymethoxydibenzalacetone. Other suitable photoinitiators that may be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The heterogeneous mass comprises enrobeable elements and discrete pieces of foam. The enrobeable elements may be a web such as, for example, nonwoven, a fibrous structure, an air-laid web, a wet laid web, a high loft nonwoven, a carded nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, an electrospun(nano-fiber) web, and layered webs that are layered combinations thereof.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination.

The enrobeable elements may be hydrophobic or hydrophilic. The enrobeable elements may be treated to be made hydrophobic. The enrobeable elements may be treated to become hydrophilic.

The constituent fibers of the heterogeneous mass may be comprised of polymers such as polyethylene, polypropylene, polyester, and blends thereof. The fibers may be spunbound fibers. The fibers may be meltblown fibers, or nanofibers. The fibers may comprise cellulose, rayon, cotton, or other natural materials or blends of polymer and natural materials. The fibers may also comprise a super absorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers may range from about 0.1 denier to about 100 denier.

In one aspect, known absorbent web materials in an as-made may be considered as being homogeneous throughout. Being homogeneous, the fluid handling properties of the absorbent web material are not location dependent, but are substantially uniform at any area of the web. Homogeneity may be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability may be accomplished without a decrease in capillarity.

The heterogeneous mass may also include superabsorbent material that imbibe fluids and form hydrogels. These materials are typically capable of absorbing large quantities of body fluids and retaining them under moderate pressures. The heterogeneous mass may include such materials dispersed in a suitable carrier such as cellulose fibers in the form of fluff or stiffened fibers.

The heterogeneous mass may include thermoplastic particulates or fibers. The materials, and in particular thermoplastic fibers, may be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g. per sq. of centimeter of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e. unbent) or crimped (i.e. bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. In a spunbond process, the fibers may be continuous. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, if used in a carded non-woven, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties—of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The heterogeneous mass may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

However structured, the total absorbent capacity of the heterogeneous mass containing foam pieces should be compatible with the design loading and the intended use of the mass. For example, when used in an absorbent article, the size and absorbent capacity of the heterogeneous mass may be varied to accommodate different uses such as incontinence pads, pantiliners, regular sanitary napkins, or overnight sanitary napkins. The heterogeneous mass may also include other optional components sometimes used in absorbent webs. For example, a reinforcing scrim may be positioned within the respective layers, or between the respective layers, of the heterogeneous mass.

The heterogeneous mass comprising open-cell foam pieces produced from the present invention may be used as an absorbent core or a portion of an absorbent core in absorbent articles, such as feminine hygiene articles, for example pads, pantiliners, and tampons; disposable diapers; incontinence articles, for example pads, adult diapers; home-care articles, for example wipes, pads, towels; and beauty care articles, for example pads, wipes, and skin care articles, such as used for pore cleaning.

The heterogeneous mass may be used as an absorbent core for an absorbent article. The absorbent core may be relatively thin, less than about 5 mm in thickness, or less than about 3 mm, or less than about 1 mm in thickness. Cores having a thickness of greater than 5 mm are also contemplated herein. Thickness may be determined by measuring the thickness at the midpoint along the longitudinal centerline of the absorbent structure by any means known in the art for doing while under a uniform pressure of 0.25 psi. The absorbent core may comprise absorbent gelling materials (AGM), including AGM fibers, as is known in the art.

The heterogeneous mass may be formed or cut to a shape, the outer edges of which define a periphery. Additionally, the heterogeneous mass may be continuous such that it may be rolled or wound upon itself, with or without the inclusion of preformed cut lines demarcating the heterogeneous mass into preformed sections.

When used as an absorbent core, the shape of the heterogeneous mass may be generally rectangular, circular, oval, elliptical, or the like. Absorbent core may be generally centered with respect to the longitudinal centerline and transverse centerline of an absorbent article. The profile of absorbent core may be such that more absorbent is disposed near the center of the absorbent article. For example, the absorbent core may be thicker in the middle, and tapered at the edges in a variety of ways known in the art.

Without being bound by theory, it is believed that one of the key technical mechanisms behind the breaking the inherent trade-off between comfort and protection/stability is the ability that HIPE offers to uniquely and strategically prescribe the stiffness and absorbent properties of the protective absorbent structure. This is enabled by the formation of the HIPE foam/enrobeable element composite structure which creates a heterogeneous mass and the creation of one or more transition zones within the absorbent structure. Enrobeable elements in the form of NW fibers become entangled within the HIPE upon which, surprisingly, the structural properties of the heterogeneous mass composite become amplified creating highly directional or biased stiffness/flexibility.

Structural testing has revealed that a differential Machine Direction (MD)-to-Cross Direction (CD) bending rigidity can be achieved in a heterogeneous mass composite absorbent core up to 20 times without any mechanical weakening by solid-state formation (SSF) and/or aperturing the heterogeneous mass absorbent structure with slots, dots, or apertures of other geometric shapes.

Without being bound by theory, it is believed that mechanical deformation of the heterogeneous mass absorbent structure combined with targeted placement of HIPE into or onto the mass of enrobeable elements to create the polymerized heterogeneous mass allows for the optimization of stiffness and flexibility for comfort and stability of the product shape, while at the same time, optimizing where absorbent is needed in the product core and chassis.

One highly relevant of application of leveraging the differential bending rigidity to create a stable product shape in the CD. By orienting stiff direction of the mass of enrobeable elements in the form of Nonwoven substrate(s) of the heterogeneous mass composite in the product CD, one create a more stable product in the CD direction. Without being bound by theory, it is believed that stiffness and resiliency in the CD direction is needed by the consumer to which she needs the product to present a larger area of coverage and offer the consumer protection as she executes motions throughout her day. This stiffness can be optimized provide her instant fit and coverage while at the same time enabling a comfortable shape that forms and moves with her due to the orientation of the less stiff direction being aligned with the product MD—providing increased conformance of the product shape from front to back.

There are several levers that are available to control the resultant stiffness of the heterogeneous mass composite, these include but are not limited to, choice of substrate (base substrate directionality), HIPE formulation (BW, cell size), and the number of transition zones. Emulsion water-to-oil ratio, transition zone size/thickness, NW substrate tension, NW-sidedness and which NW the emulsion is laid down upon may also influence on resultant composite flexibility.

Traditional in-market HIPE foam comprises two layers has isotropic stiffness properties in the plane of product. A layer of HIPE foam which is the absorbent layer of the heterogeneous mass composite is isotropic in stiffness as well however when the layer of HIPE is laid down on a NW substrate at the time of making, prior to polymerization, the HIPE enrobes portions of the NW substrates and enhances the stiffness of both the NW and the post-polymerization HIPE foam. Surprisingly, as shown in the table below, the resultant bending rigidity of the heterogeneous mass absorbent composite is greater than the sum of the bending rigidity of the NW substrate and the HIPE foam layer when added separately.

Table 1 shows that the bending rigidity for the MD and CD directions of the component materials (items 1 & 2) does not equate to the resultant bending rigidity for the heterogeneous mass absorbent composite (item 3).

TABLE 1

Bending rigidity nonwoven, HIPE foam layer, and Heterogeneous Mass Absorbent Composite

| Description | Item # | Bending Rigidity (gf*cm^2/cm) MD | CD | MD/CD |
|---|---|---|---|---|
| NW-AQL 60-gsm | 1 | 0.19 | 0.09 | 2.11 |
| HIPE Foam layer with 27:1 oil to water ratio | 2 | 0.11 | 0.12 | 0.92 |
| Invention D: Heterogeneous mass absorbent Composite | 3 | 2.45 | 0.53 | 4.62 |
| Sum of bending rigidity | 1 + 2 | 0.30 | 0.21 | |
| Ratio Composite over component sum Rigidity | 3/(1 + 2) | 8.16 | 2.52 | |

As calculated above, the bending rigidity of the heterogeneous mass absorbent composite is more than 8 times or 8× and 2.5× stiffer in Machine Direction and Cross Direction respectively when compare to the sum of the individual component parts.

Differential bending rigidity is further amplified by creating a stratum comprising more than one planar nonwoven to which the open cell foam is enrobed. The open cell foam enrobes a portion of each planar nonwoven creating an area of transition between each nonwoven planar and the open cell foam along the vertical axis. By placing the emulsion in contact with a first planar layer of nonwoven fibers on a first surface of the emulsion and a second planar layer of nonwovens fibers on a Table 1 shows that the differential rigidity MD to CD is roughly 4.5× for a single transition zone heterogeneous mass absorbent composite material (created by one planar nonwoven). Table 2 shows that a 55-gsm Spunlace-HIPE-55-gsm Spunlace sandwich the differential bending rigidity is greater than 20× MD to CD.

| Composite Description | Bending Rigidity (gf*cm^2/cm) | | |
|---|---|---|---|
| | MD | CD | MD/CD |
| Invention A: 55 gsm nonwoven with HIPE | 9.456 | 0.442 | 21.4 |
| Invention B: 55 gsm nonwoven with HIPE | 11.82 | 0.641 | 18.4 |

Table 3 shows how the differential bending rigidity for a single transition zone of similar construction like shown in Table 2 can drop the differential properties roughly 5× of the composite structure by removing a transition zone.

TABLE 2

Single transition of similar construction

| Composite Description | Bending Rigidity (gf*cm^2/cm) | | |
|---|---|---|---|
| | MD | CD | MD/CD |
| Invention F: 55 gsm nonwoven with HIPE | 2.552 | 0.541 | 4.7 |

Magnitude of bending rigidity can be controlled with emulsion cell size. Data in Table 4 shows larger cell sizes tend to create structures that are less flexible than the standard cell size counterpart.

TABLE 3

Emulsion cell size impact on bending rigidity

| Composite Description | Bending Rigidity (gf*cm^2/cm) | | |
|---|---|---|---|
| | MD | CD | MD/CD |
| Invention C: 60 gsm nonwoven with HIPE | >14 | 2.271 | |
| Invention E: 60 gsm nonwoven with HIPE | 4.340 | 1.028 | 4.2 |

As shown in the tables above, the absorbent structure may exhibit exhibits a Cross Direction bending rigidity between 0.3 gf*cm^2/cm and 0.6 gf*cm^2/cm and a Machine Direction bending rigidity between 1.5 gf*cm^2/cm and 14 gf*cm^2/cm. The absorbent structure may exhibit a Cross Direction bending rigidity between 0.5 gf*cm^2/cm and 1 gf*cm^2/cm and a Machine Direction bending rigidity between 2 gf*cm^2/cm and 12 gf*cm^2/cm. As shown in in the tables above, the absorbent structure may exhibit a Cross Direction bending rigidity between 0.2 gf*cm^2/cm and 1.6 gf*cm^2/cm, such as, for example between 0.3 gf*cm^2/cm and 1.4 gf*cm^2/cm, between 0.3 gf*cm^2/cm and 1.2 gf*cm^2/cm, between 0.3 gf*cm^2/cm and 1.0 gf*cm^2/cm, between 0.3 gf*cm^2/cm and 0.8 gf*cm^2/cm, or between 0.3 gf*cm^2/cm and 0.6 gf*cm^2/cm. As shown in the tables above, the absorbent structure may exhibit a Machine Direction bending rigidity between 1.5 gf*cm^2/cm and 15 gf*cm^2/cm, such as, for example between 1.5 gf*cm^2/cm and 12 gf*cm^2/cm, between 2 gf*cm^2/cm and 9 gf*cm^2/cm, between 2 gf*cm^2/cm and 6 gf*cm^2/cm, between 2 gf*cm^2/cm and 5 gf*cm^2/cm, or between 2 gf*cm^2/cm and 4 gf*cm^2/cm.

As shown in the tables above, the absorbent structure may exhibit a Machine Direction bending rigidity to Cross Direction bending rigidity ratio of between 2 to 25. The absorbent structure may exhibit a Machine Direction bending rigidity to Cross Direction bending rigidity ratio of between 5 to 15.

As previously discussed, the inherent contradiction that has been facing designers of absorbent articles is offering superior protection while providing garment-like comfort. Surprisingly, by creating a heterogeneous mass absorbent composite using a nonwoven substrate and an open cell foam, one can create a thin and absorbent core technology that exhibits desirable differential bending rigidity (MD to CD direction). The differential flexibility products may have improved conformance and follow the consumer's body better due the strategic tuning of stiffness and flexibility.

For the materials presented in Tables 2 through 4 the bunched compression properties are provided for these materials in two different directions in a weaker MD fiber orientation and with a stronger CD fiber orientation.

The absorbent structure single stratum may serve as any portion of an absorbent article. The absorbent structure single stratum may serve as the absorbent core of an absorbent article. The absorbent structure single stratum may serve as a portion of the absorbent core of an absorbent article. More than one absorbent structure single stratum may be combined wherein each absorbent structure single stratum differs from at least one other absorbent structure single stratum in either the choice of enrobeable elements or by a characteristic of its open-cell foam pieces. The different two or more absorbent structures single stratums may be combined to form an absorbent core. The absorbent article may further comprise a topsheet and a backsheet.

The absorbent structure single stratum may be used as a topsheet for an absorbent article. The absorbent structure single stratum may be combined with an absorbent core or may only be combined with a backsheet.

The absorbent structure single stratum may be combined with any other type of absorbent layer such as, for example, a storage or acquisition layer comprising a layer of cellulose, a layer comprising superabsorbent gelling materials, a layer of absorbent airlaid fibers, or a layer of absorbent foam. Other absorbent layers not listed are contemplated herein.

The absorbent structure single stratum may be utilized by itself for the absorption of fluids without placing it into an absorbent article.

An absorbent article may comprise a liquid pervious topsheet. The topsheet suitable for use herein may comprise wovens, non-wovens, and/or three-dimensional webs of a liquid impermeable polymeric film comprising liquid permeable apertures. The topsheet for use herein may be a single layer or may have a multiplicity of layers. For example, the wearer-facing and contacting surface may be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. Nos. 3,929,135, 4,151,240, 4,319,868, 4,324,426, 4,343,314, 4,591,523, 4,609,518, 4,629,643, 4,695,422 or WO 96/00548.

As shown in FIG. 1, the absorbent article 10 has a body contacting surface 12 in the form of a topsheet 14, a backsheet 16, and an absorbent core 18 between the topsheet 14 and the backsheet 16. The absorbent article 10 of FIG. 1 may have a lotion composition 22 applied thereto. The lotion composition 22 may be applied in parallel stripes to the inner surface of the backsheet 16. The absorbent article 10 of FIG. 1 may have a secondary topsheet (not shown).

The absorbent article may comprise any known or otherwise effective topsheet, such as one which is compliant, soft feeling, and non-irritating to the wearer's body. Suitable topsheet materials include a liquid pervious material that is oriented towards and contacts the body of the wearer permitting bodily discharges to rapidly penetrate through it without allowing fluid to flow back through the topsheet to the skin of the wearer. The topsheet, while being capable of allowing rapid transfer of fluid through it, also provides for the transfer or migration of the lotion composition onto an external or internal portion of a wearer's body. A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof, as is well known in the art of making catamenial products such as sanitary napkins, pantiliners, incontinence pads, and the like.

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling.

The catamenial device of the present invention also comprises a backsheet. The backsheet can be any known or otherwise effective backsheet material, provided that the backsheet prevents external leakage of exudates absorbed and contained in the catamenial device. Flexible materials suitable for use as the backsheet include, but are not limited to, woven and nonwoven materials, laminated tissue, polymeric films such as thermoplastic films of polyethylene and/or polypropylene, composite materials such as a film-coated nonwoven material, or combinations thereof, as is well known in the art of making catamenial products such as sanitary napkins, pantiliners, incontinence pads, and the like.

The catamenial device also comprises an absorbent core. The absorbent core is typically positioned between the topsheet and the backsheet. As used herein, the term "absorbent core" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user.

Table 5 represents additional inventive examples as well as the ones listed above. As shown in the table, the absorbent structure may exhibit a Cross Direction bending rigidity between 0.3 gf*cm^2/cm and 1.6 gf*cm^2/cm and a Machine Direction bending rigidity between 1.5 gf*cm^2/cm and 15 gf*cm^2/cm. The MD and CD bending rigidities translate to a Machine Direction bending rigidity to Cross Direction bending rigidity ratio of between 2 to 25, such as, for example 3, 4, 5, 6, 7, 8, 9, 10, 11, 12, 13, 14, 15, 16, 17, 18, 19, 20, 21, 22, 23, and 24.

| Composite Description | Bending Rigidity (gf*cm^2/cm) | | |
|---|---|---|---|
| | MD | CD | MD/CD |
| Invention A: 55 gsm nonwoven with HIPE plus 55 gsm nonwoven | 9.456 | 0.442 | 21.4 |
| Invention B: 55 gsm nonwoven with HIPE plus 55 gsm nonwoven | 11.82 | 0.641 | 18.4 |
| Invention C: 60 gsm nonwoven with HIPE plus 55 gsm nonwoven | >14 | 2.271 | |
| Invention D: Heterogeneous mass absorbent Composite | 2.45 | 0.53 | 4.62 |
| Invention E: 60 gsm nonwoven with HIPE plus 55 gsm nonwoven | 4.34 | 1.028 | 4.2 |
| Invention F: 55 gsm nonwoven with HIPE | 2.552 | 0.541 | 4.7 |
| Example G: 60 gsm nonwoven with HIPE plus 55 gsm nonwoven | 3.56 | 0.7 | 5.09 |
| Example H: 60 gsm nonwoven with HIPE | 3.02 | 0.53 | 5.68 |
| Example I: 45 gsm nonwoven with HIPE | 2.12 | 0.37 | 5.69 |
| Example J: 60 gsm nonwoven with HIPE | 2.39 | 0.4 | 5.96 |
| Example K: 60 gsm nonwoven with HIPE | 2.61 | 0.35 | 7.4 |

As shown in Table 5, the absorbent structure may exhibit a Cross Direction bending rigidity between 0.2 gf*cm^2/cm and 1.6 gf*cm^2/cm, such as, for example between 0.3 gf*cm^2/cm and 1.4 gf*cm^2/cm, between 0.3 gf*cm^2/cm and 1.2 gf*cm^2/cm, between 0.3 gf*cm^2/cm and 1.0 gf*cm^2/cm, between 0.3 gf*cm^2/cm and 0.8 gf*cm^2/cm, or between 0.3 gf*cm^2/cm and 0.6 gf*cm^2/cm. The absorbent structure may exhibit a Machine Direction bending rigidity between 1.5 gf*cm^2/cm and 15 gf*cm^2/cm, such as, for example between 1.5 gf*cm^2/cm and 12 gf*cm^2/cm, between 2 gf*cm^2/cm and 9 gf*cm^2/cm, between 2 gf\*cmˆ2/cm and 6 gf\*cmˆ2/cm, between 2 gf\*cmˆ2/cm and 5 gf\*cmˆ2/cm, or between 2 gf\*cmˆ2/cm and 4 gf\*cmˆ2/cm.

TABLE 6

MD/CD Bending for in-market cores

| Composite Description | Bending Rigidity (gf\*cmˆ2/cm) | | |
|---|---|---|---|
| | MD | CD | MD/CD |
| Marketed core construction 1 | 1.60 | 1.67 | 0.96 |
| Marketed core construction 2 | 0.92 | 0.52 | 1.79 |

Table 6 includes the MD and CD bending rigidity for two currently in-market cores. As shown in the table, the MD/CD ratio is less than two for both cores.

Figure 2:
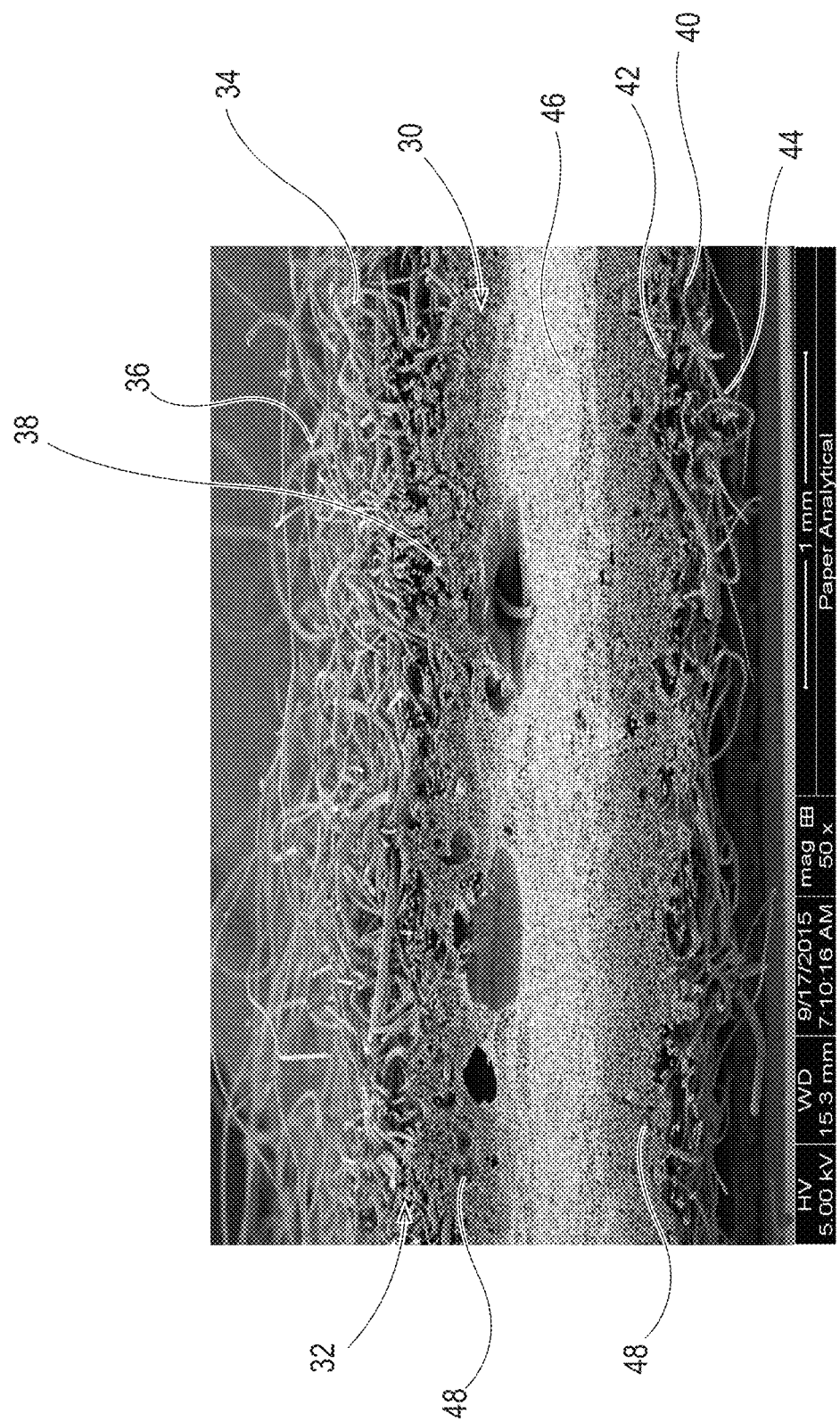
FIG. 2 is an SEM micrograph of one embodiment of the invention.

FIG. 2 is an SEM micrograph of an embodiment of the invention. As shown in FIG. 2, the absorbent stratum 30 is a heterogeneous mass 32 comprising a first planar nonwoven 34 having a first surface 36 and a second surface 38 and a second planar nonwoven 40 having a first surface 42 and a second surface 44. An open cell foam piece 46 enrobes a portion of the first planar nonwoven 34 and a portion of the second planar nonwoven 40. Specifically, the open cell foam piece 46 enrobes enrobeable elements 48 in both the second surface 38 of the first planar nonwoven 34 and the first surface 42 of the second planar nonwoven 40.

Examples

A. An absorbent article comprising a topsheet, a backsheet, and an absorbent core comprising an absorbent structure, wherein the absorbent structure exhibits a Cross Direction bending rigidity between 0.3 gf\*cmˆ2/cm and 1.6 gf\*cmˆ2/cm and a Machine Direction bending rigidity between 1.5 gf\*cmˆ2/cm and 14 gf\*cmˆ2/cm.

B. The absorbent article according to paragraph A, wherein the absorbent structure exhibits a Machine Direction bending rigidity to Cross Direction bending rigidity ratio of between 2 to 25.

C. The absorbent article according to paragraph A or B, wherein the absorbent structure exhibits a Cross Direction bending rigidity between 0.5 gf\*cmˆ2/cm and 1 gf\*cmˆ2/cm and a Machine Direction bending rigidity between 2 gf\*cmˆ2/cm and 12 gf\*cmˆ2/cm.

D. The absorbent article according to any of paragraphs A-C, wherein the absorbent structure exhibits a Machine Direction bending rigidity to Cross Direction bending rigidity ratio of between 5 to 15.

E. The absorbent article according to any of paragraphs A-D, wherein the absorbent structure comprises one or more nonwoven fiber.

F. The absorbent article according to any of paragraphs A-E, wherein the absorbent structure comprises open cell foam.

G. The absorbent article according to any of paragraphs A-F, wherein the absorbent core comprises superabsorbent.

H. The absorbent article according to any of paragraphs A-G, wherein the absorbent structure is combined with one or more layers to create an absorbent core.

I. An Absorbent article comprising a topsheet, a backsheet, and an absorbent core comprising an absorbent structure, wherein the absorbent structure exhibits a Machine Direction bending rigidity to Cross Direction bending rigidity ratio of between 2 to 25.

J. The absorbent article according to paragraph I, wherein the absorbent structure exhibits a bending rigidity in the CD direction between 0.5 gf\*cmˆ2/cm and 1 gf\*cmˆ2/cm and a bending rigidity in the MD direction between 2 gf\*cmˆ2/cm and 12 gf\*cmˆ2/cm.

K. The absorbent article according to paragraph I or J, wherein the absorbent core exhibits a Machine Direction bending rigidity to Cross Direction bending rigidty ratio of 5 to 15.

L. The absorbent article according to any of paragraphs I-K, wherein the absorbent structure comprises one or more nonwoven fiber.

M. The absorbent article according to any of paragraphs I-L, wherein the absorbent structure comprises open cell foam.

N. The absorbent article according to any of paragraphs I-M, wherein the absorbent core comprises superabsorbent.

O. The absorbent article according to any of paragraphs I-N, wherein the absorbent structure is combined with one or more layers to create an absorbent core.

P. An Absorbent article comprising a topsheet, a backsheet, and an absorbent core comprising an absorbent structure, wherein the absorbent structure exhibits a Cross Direction bending rigidity between 0.3 gf\*cmˆ2/cm and 1.6 gf\*cmˆ2/cm and a Machine Direction bending rigidity between 1.5 gf\*cmˆ2/cm and 14 gf\*cmˆ2/cm, wherein the absorbent structure comprises a heterogeneous mass composite comprising enrobeable elements and open cell foam.

Q. The absorbent article according to paragraph P, wherein the enrobeable elements comprises of two or more nonwovens.

R. The absorbent article according to paragraph P or Q, wherein the two or more nonwovens comprise of a first nonwoven planar sheet and a second nonwoven planar sheet, wherein the nonwoven of the first nonwoven planar sheet is different from nonwoven of the second nonwoven planar sheet, wherein the open cell foam enrobes a portion of the first nonwoven planar sheet and a portion of the second nonwoven planar sheet.

S. The absorbent article according to any of paragraphs P-R, wherein the enrobeable elements are selected from the group consisting of a nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are al wed combinations thereof.

Kawabata Method

Bending rigidity is measured using a Kawabata Evaluation System KES-FB2-A, Pure Bend Tester Sensor (available from Kato Tech Co., Japan) and is reported in gfcm$^2$/cm for both machine direction(MD) and cross direction (CD). The instrument is calibrated as per the manufacturer's instructions. All testing is performed at about 23° C.±2 C.° and about 50%±2% relative humidity.

The Bending Rigidity is measured as the slope between 0.5 cm$^{-1}$ and 1.5 cm$^{-1}$ and −0.5 cm$^{-1}$ and −1.5 cm$^{-1}$. Instrument conditions are set as Maximum curvature: K max=±2.5 cm$^{-1}$, Cycles=1, Bending rate=2.5 cm$^{-1}$/sec. The sensitivity is set appropriately for the sample's rigidity but a nominal value of 50 is representative.

Articles or materials are preconditioned at about 23° C.±2 C.° and about 50%±2% relative humidity for 2 hours prior to testing. If the sample is an article, remove the layer of interest from the article using cryo-spray as needed. The "Standard Condition" specimen size is 20.0 cm×20.0 cm, and should be used when available. If the standard size is not available cut the width of the specimen to the nearest cm (e.g., if the width is 17.4 cm, cut to 17.0 cm) then use the "Optional Condition" setting on the instrument to specify the width to the nearest cm. If necessary based on the rigidity of the specimen, the width can be reduced to allow measurement of the specimen within the instruments capability. A total of six (6) specimens are prepared, three for testing in each MD and CD direction.

Insert the specimen into the instrument, such that the bending deformation is applied to the width direction. Start the test and record Bending Rigidity to the nearest 0.01 gfcm$^2$/cm. Repeat testing for all specimens. Calculate Bending Rigidity as the geometric mean of three CD specimens and three MD specimens and report separately to the nearest 0.01 gfcm$^2$/cm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a topsheet, a backsheet, and an absorbent core comprising an absorbent structure, wherein the absorbent structure comprises a nonwoven fabric and discrete pieces of open cell foam that have been formed about fibers of the nonwoven fabric so as to enrobe them, and the absorbent structure exhibits a Cross Direction bending rigidity between 0.3 gf*cm^2/cm and 1.6 gf*cm^2/cm and a Machine Direction bending rigidity between 1.5 gf*^2/cm and 14 gf*cm^2/cm.

2. The absorbent article of claim 1, wherein the absorbent structure exhibits a Machine Direction bending rigidity to Cross Direction bending rigidity ratio of between 2 to 25.

3. The absorbent article of claim 1, wherein the absorbent structure exhibits a Cross Direction bending rigidity between 0.5 gf*cm^2/cm and 1 gf*cm^2/cm and a Machine Direction bending rigidity between 2 gf*cm^2/cm and 12 gf*cm^2/cm.

4. The absorbent article of claim 1, wherein the absorbent structure exhibits a Machine Direction bending rigidity to Cross Direction bending rigidity ratio of between 5 to 15.

5. The absorbent article of claim 1, wherein the absorbent core comprises superabsorbent.

6. The absorbent article of claim 1, wherein the absorbent structure is combined with one or more layers to create the absorbent core.

7. An absorbent article comprising a topsheet, a backsheet, and an absorbent core comprising an absorbent structure, wherein the absorbent structure comprises a nonwoven fabric and discrete pieces of open cell foam that have been formed about fibers of the nonwoven fabric so as to enrobe them, and the absorbent structure exhibits a Machine Direction bending rigidity to Cross Direction bending rigidity ratio of between 2 to 25.

8. The absorbent article of claim 7, wherein the absorbent structure exhibits a bending rigidity in the CD direction between 0.5 gf*cm^2/cm and 1 gf*cm^2/cm and a bending rigidity in the MD direction between 2 gf*cm^2/cm and 12 gf*cm^2/cm.

9. The absorbent article of claim 7, wherein the absorbent core exhibits a Machine Direction bending rigidity to Cross Direction bending rigidity ratio of 5 to 15.

10. The absorbent article of claim 7, wherein the absorbent core comprises superabsorbent.

11. The absorbent article of claim 7, wherein the absorbent structure is combined with one or more layers to create the absorbent core.

* * * * *